United States Patent
Li et al.

(10) Patent No.: US 10,876,019 B2
(45) Date of Patent: Dec. 29, 2020

(54) POLYORGANOSILOXANE COMPOSITIONS CONTAINING A 2-SUBSTITUTED-1-ALKYNYL-1-CYCLOHEXANOL USEFUL AS A HYDROSILYLATION REACTION INHIBITOR

(71) Applicant: Dow Silicones Corporation, Midland, MI (US)

(72) Inventors: Zhanjie Li, Midland, MI (US); Zhenbin Niu, Midland, MI (US)

(73) Assignee: Dow Silicones Corporation, Midland, MI (US)

( * ) Notice: Subject to any disclaimer, the term of this patent is extended or adjusted under 35 U.S.C. 154(b) by 0 days.

(21) Appl. No.: 16/635,336

(22) PCT Filed: Oct. 17, 2018

(86) PCT No.: PCT/US2018/056173
§ 371 (c)(1),
(2) Date: Jan. 30, 2020

(87) PCT Pub. No.: WO2019/079365
PCT Pub. Date: Apr. 25, 2019

(65) Prior Publication Data
US 2020/0377759 A1 Dec. 3, 2020

Related U.S. Application Data

(60) Provisional application No. 62/574,393, filed on Oct. 19, 2017.

(51) Int. Cl.
*C09D 183/04* (2006.01)
*C08L 83/04* (2006.01)
*C07C 35/17* (2006.01)

(52) U.S. Cl.
CPC ............ *C09D 183/04* (2013.01); *C07C 35/17* (2013.01); *C08L 83/04* (2013.01); *C07C 2601/14* (2017.05); *C08L 2205/025* (2013.01); *C08L 2205/03* (2013.01)

(58) Field of Classification Search
CPC ......... C08L 83/04; C08G 77/12; C08G 77/20; C07C 35/17; C09D 183/04; B32B 27/283
See application file for complete search history.

(56) References Cited

U.S. PATENT DOCUMENTS

| | | |
|---|---|---|
| 2,919,281 A | 12/1959 | Chodroff et al. |
| 3,159,601 A | 12/1964 | Ashby |
| 3,220,972 A | 11/1965 | Lamoreaux |
| 3,296,291 A | 1/1967 | Chalk et al. |
| 3,419,593 A | 12/1968 | Willing |
| 3,516,946 A | 6/1970 | Modic |
| 3,814,730 A | 6/1974 | Karstedt |
| 3,989,668 A | 11/1976 | Lee et al. |
| 4,604,232 A * | 8/1986 | Wiegers ............... C07C 45/512 424/69 |
| 4,766,176 A | 8/1988 | Lee et al. |
| 4,784,879 A | 11/1988 | Lee et al. |
| 5,017,654 A | 5/1991 | Togashi et al. |
| 5,036,117 A | 7/1991 | Chung et al. |
| 5,175,325 A | 12/1992 | Brown et al. |
| 5,625,023 A | 4/1997 | Chung et al. |
| 6,200,581 B1 | 3/2001 | Lin et al. |
| 6,586,535 B1 | 7/2003 | Clark et al. |
| 6,642,184 B1 | 11/2003 | De Ridder |
| 6,806,339 B2 | 10/2004 | Cray et al. |
| 7,378,482 B2 | 5/2008 | Asch et al. |
| 7,429,636 B2 | 9/2008 | Asch et al. |
| 7,906,605 B2 | 3/2011 | Cray et al. |
| 8,722,153 B2 | 5/2014 | Ekeland |
| 8,933,177 B2 | 1/2015 | Hori et al. |
| 9,120,935 B2 | 9/2015 | Marrot et al. |
| 9,562,149 B2 | 2/2017 | Cray et al. |
| 2003/0088042 A1 | 5/2003 | Griswold et al. |
| 2004/0254274 A1 | 12/2004 | Griswold |
| 2005/0038188 A1 | 2/2005 | Ahn |
| 2006/0074212 A1 | 4/2006 | Chapman et al. |
| 2007/0289495 A1 | 12/2007 | Cray et al. |
| 2010/0144960 A1 | 6/2010 | Cray et al. |
| 2011/0287267 A1 | 11/2011 | Ekeland |
| 2016/0009865 A1 | 1/2016 | Jiang et al. |
| 2016/0053056 A1 | 2/2016 | Gould et al. |
| 2018/0056173 A1 | 3/2018 | Lasar, IV |

FOREIGN PATENT DOCUMENTS

| | | |
|---|---|---|
| CN | 104151839 | 11/2014 |
| EP | 0347895 B | 12/1989 |
| EP | 0556023 | 8/1993 |
| GB | 627453 | 8/1949 |
| JP | 2000178201 | 6/2000 |
| JP | 2000178210 | 6/2000 |

OTHER PUBLICATIONS

Search report from corresponding China 201880050625.5 application, dated Jul. 22, 2020.
Search report from corresponding Japan 2020-504671 application, dated Sep. 23, 2020.
Dao, Hydromethylation of Unactivated Olefins. Journal of the American Chemical Society. May 18, 2015.
Kagawa et al., Rearrangement of Cyclic Ethynylcarbinols III. A Few Supplementary Reaction with Monocyclic and Bicyclic Terpenoids 1961 391-403.

* cited by examiner

*Primary Examiner* — Kuo Liang Peng
(74) *Attorney, Agent, or Firm* — Catherine U. Brown

(57) ABSTRACT

A hydrosilylation curable composition includes a new 2-substituted-1-alkynyl-1-cyclohexanol as an inhibitor. The hydrosilylation curable composition is useful for preparing release coatings for packaging applications.

18 Claims, 1 Drawing Sheet

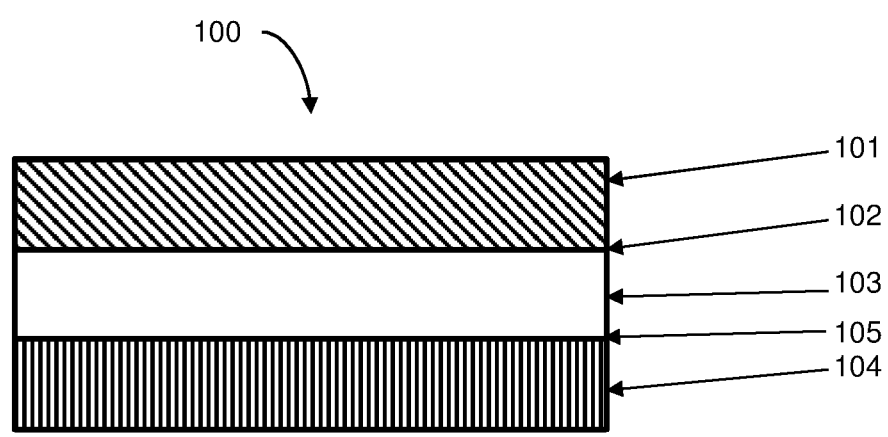

POLYORGANOSILOXANE COMPOSITIONS CONTAINING A 2-SUBSTITUTED-1-ALKYNYL-1-CYCLOHEXANOL USEFUL AS A HYDROSILYLATION REACTION INHIBITOR

CROSS REFERENCE TO RELATED APPLICATIONS

This application is a U.S. national stage filing under 35 U.S.C. § 371 of PCT Application No. PCT/US2018/056173 filed on Oct. 17, 2018, currently pending, which claims the benefit of U.S. Provisional Patent Application No. 62/574,393 filed Oct. 19, 2017 under 35 U.S.C. § 119 (e). PCT Application No. PCT/US2018/056173 and U.S. Provisional Patent Application No. 62/574,393 are hereby incorporated by reference.

TECHNICAL FIELD

A 2-substituted-1-alkynyl-1-cyclohexanol is useful as a hydrosilylation reaction inhibitor. The inhibitor is useful in a curable composition. The curable composition can be a release coating composition suitable for coating on a substrate such as a film or paper and curing via hydrosilylation reaction to form a release liner.

BACKGROUND

Hydrosilylation reaction curable compositions useful for preparing release coatings typically include a polyorganosiloxane with silicon bonded groups having terminal aliphatic unsaturation, a polyorganohydrogensiloxane, a platinum catalyst, and an acetylenic alcohol as an inhibitor to control reaction rate. One such inhibitor is 1-ethynyl-1-cyclohexanol (ETCH).

However, ETCH has disadvantages. ETCH has a melting point of 33° C. at 1 atmosphere, making it a solid at room temperature (RT) of 25° C. Therefore, to formulate ETCH into a release coating composition, the ETCH must first be heated. And, to avoid crystallizing ETCH out of the composition, the other starting materials, such as the polyorganosiloxane with silicon bonded groups having terminal aliphatic unsaturation may also need to be heated.

The platinum catalyst and inhibitor work together to afford acceptable working times of the release coating compositions. Release coating compositions are typically supplied to coating equipment from a coating bath. The coating bath is supplied to the coating equipment to form a thin film (e.g., the composition is supplied from a bulk in a container to form a thin film of release coating composition on rolls in a roll coater). Working time can be divided into bulk bath life and thin film bath life. Bulk bath life is the time when viscosity of the coating bath doubles compared to the initial viscosity of the coating bath at 40° C. Thin film bath life denotes the time when a 2 mil coating film is cured at RT. If bulk bath life of a release coating composition is too short, there is a risk of gelling the coating bath, piping, or other parts of the coating equipment. If the thin film bath life is too short, there is a risk of gelling the portions of the coating equipment with the thin film, e.g., the coater rolls. Long bath life seemingly can be easily achieved by lowering the platinum level or increasing the inhibitor level. However, with either increasing inhibitor content or lowering platinum content, the release coating composition to cure too slowly, such that when the composition is coated on a substrate, insufficient cure of the composition in the coating equipment may cause the resulting release coating to have poor rub off resistance. Therefore, the catalyst and inhibitor and their relative amounts are selected to achieve desired fast cure and appropriate bulk bath life and thin film bath life. While ETCH in combination with certain platinum catalysts can produce appropriate bulk bath life and thin film bath life for release coating applications, a relatively high level of expensive platinum catalyst (such as Karstedt's catalyst) is required to achieve desired cure properties while maintaining sufficient bulk bath life and thin film bath life.

There is an industry need to produce hydrosilylation reaction curable compositions including an inhibitor that does not precipitate or crystallize out of the composition under normal storage and use temperatures. There is a need in the release coating industry to provide a release coating composition that has one or more of the following properties: good bulk bath life, good thin film bath life, and curability to form a release coating on a substrate that has good rub off resistance or other properties. And there is a desire in the industry to reduce costs of manufacture of release coatings.

SUMMARY

A curable composition comprises:
A) a polyorganosiloxane having an average, per molecule, of at least two silicon bonded groups having terminal aliphatic unsaturation;
B) a polyorganohydrogensiloxane having an average, per molecule, of at least 2 silicon bonded hydrogen atoms;
with the provisos that
when starting material A) has an average, per molecule, of 2 silicon bonded hydrocarbon groups having terminal aliphatic unsaturation, then starting material B) has an average, per molecule, of greater than 2 silicon bonded hydrogen atoms; and
when starting material B) has an average, per molecule, of 2 silicon bonded hydrogen atoms, then starting material A) has an average, per molecule, of greater than 2 silicon bonded hydrocarbon groups having terminal aliphatic unsaturation;
C) a hydrosilylation-reaction catalyst; and
D) a 2-substituted-1-alkynyl-1-cyclohexanol. The polyorganosiloxane composition can be coated on a substrate and cured via hydrosilylation reaction to prepare a coated substrate such as a release liner.

The 2-substituted-1-alkynyl-1-cyclohexanol is useful as an inhibitor in hydrosilylation reaction curable compositions. The 2-substituted-1-alkynyl-1-cyclohexanol may have formula:

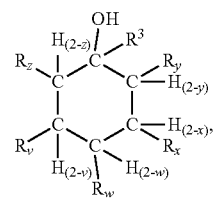

where $R^3$ is an alkynyl group having at least 2 carbon atoms, each R is an independently selected monovalent hydrocarbon group having at least 1 carbon atom, subscript v is 0 to 2, subscript w is 0 to 2, subscript x is 0 to 2, subscript y is 0 to 2, subscript z is 0 to 2, with the provisos that a quantity (v+w+x+y+z)>1, and a quantity (y+z) is 1 to 4.

BRIEF DESCRIPTION OF THE DRAWINGS

FIG. 1 shows a partial cross section of a release liner 100. The release liner comprises a release coating 101 prepared by curing a release coating composition described herein on a first surface 102 of a film substrate 103. The release liner 100 further includes a carrier 104 mounted to an opposing surface 105 of the film substrate 103.

DETAILED DESCRIPTION OF THE INVENTION

The curable composition described herein comprises: A) a polyorganosiloxane containing at least two silicon-bonded aliphatically unsaturated groups per molecule; B) a polyorganohydrogensiloxane having an average, per molecule, of at least 2 silicon bonded hydrogen atoms; with the provisos that when starting material A) has an average, per molecule, of 2 silicon bonded hydrocarbon groups having terminal aliphatic unsaturation, then starting material B) has an average, per molecule, of greater than 2 silicon bonded hydrogen atoms; and when starting material B) has an average, per molecule, of 2 silicon bonded hydrogen atoms, then starting material A) has an average, per molecule, of greater than 2 silicon bonded hydrocarbon groups having terminal aliphatic unsaturation; C) a hydrosilylation-reaction catalyst; and D) a 2-substituted-1-alkynyl-1-cyclohexanol.

Starting material A) in the curable composition is a a polyorganosiloxane containing at least two silicon-bonded aliphatically unsaturated groups per molecule; alternatively a polyorganosiloxane having an average, per molecule, of at least two silicon bonded groups having terminal aliphatic unsaturation. This polyorganosiloxane may be linear, branched, partly branched, cyclic, resinous (i.e., have a three-dimensional network), or may comprise a combination of different structures. The polyorganosiloxane may have average formula: $R^4_a SiO_{(4-a)/2}$,
where each $R^4$ is independently selected from a monovalent hydrocarbon group or a monovalent halogenated hydrocarbon group, with the proviso that in each molecule, at least two of $R^4$ include terminal aliphatic unsaturation, and where subscript a is selected such that 0<a≤3.2. The average formula above for the polyorganosiloxane may be alternatively written as $(R^4_3 SiO_{1/2})_b (R^4_2 SiO_{2/2})_c (R^4 SiO_{3/2})_d (SiO_{4/2})_e$, where $R^4$ is defined above, and subscripts b, c, d, and e are each independently from ≥0 to ≤1, with the proviso that a quantity (b+c+d+e)=1. One of skill in the art understands how such M, D, T, and Q units and their molar fractions influence subscript a in the average formula above. T units (indicated by subscript d), Q units (indicated by subscript e) or both, are typically present in polyorganosiloxane resins, whereas D units, indicated by subscript c, are typically present in polyorganosiloxane polymers (and may also be present in polyorganosiloxane resins).

Each $R^4$ is independently selected, as introduced above, and may be linear, branched, cyclic, or combinations thereof. Cyclic hydrocarbon groups encompass aryl groups as well as saturated or non-conjugated cyclic groups. Aryl groups may be monocyclic or polycyclic. Linear and branched hydrocarbon groups may independently be saturated or unsaturated. One example of a combination of a linear and cyclic hydrocarbon group is an aralkyl group.

Halogenated hydrocarbon groups are hydrocarbon groups having one or more hydrogen atoms replaced (i.e., substituted) with a halogen atom such as chlorine, fluorine, bromine or iodine.

Suitable monovalent hydrocarbon groups are exemplified by alkyl groups such as methyl, ethyl, propyl (e.g., isopropyl and/or n-propyl), butyl (e.g., isobutyl, n-butyl, tert-butyl, and/or sec-butyl), pentyl (e.g., isopentyl, neopentyl, and/or tert-pentyl), cyclohexyl, hexyl, heptyl, octyl, nonyl, and decyl, and branched alkyl groups of 6 or more carbon atoms; alkenyl groups such as vinyl, allyl, propenyl, isopropenyl, butenyl, isobutenyl, pentenyl, heptenyl, hexenyl, and cyclohexenyl; aryl groups such as phenyl, tolyl, xylyl, and naphthyl; aralkyl groups such as benzyl and phenethyl. Suitable monovalent halogenated hydrocarbon groups are exemplified by halogenated alkyl groups such as 3-chloropropyl, 2-bromoethyl, fluoromethyl, 2-fluoropropyl, and 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl, 2,2-difluorocyclopropyl, 2,3-difluorocyclobutyl, 3,4-difluorocyclohexyl, and 3,4-difluoro-5-methylcycloheptyl, chloromethyl, 2-dichlorocyclopropyl, and 2,3-dichlorocyclopentyl. Halogenated aryl groups for $R^4$ are exemplified by, but not limited to, the aryl groups described above where one or more hydrogen atoms is replaced with a halogen atom, such as F or Cl. For example, chlorobenzyl and fluorobenzyl are suitable halogenated aryl groups. Alternatively, each $R^4$ is a monovalent hydrocarbon group.

In each molecule of A) the polyorganosiloxane, at least two of $R^4$ include terminal aliphatic unsaturation. Each $R^4$ including terminal aliphatic unsaturation may be independently selected from an alkenyl group and an alkynyl group. "Alkenyl" means a branched or unbranched, monovalent hydrocarbon group having one or more carbon-carbon double bonds. Alkenyl is exemplified by, but not limited to, vinyl, allyl, and hexenyl. The alkenyl group may have from 2 to 30 carbon atoms, alternatively from 2 to 24 carbon atoms, alternatively from 2 to 20 carbon atoms, alternatively from 2 to 12 carbon atoms, alternatively from 2 to 10 carbon atoms, alternatively from 2 to 6 carbon atoms. "Alkynyl" means a branched or unbranched, monovalent hydrocarbon group having one or more carbon-carbon triple bonds. Alkynyl is exemplified by, but not limited to, ethynyl, propynyl, and butynyl. The alkynyl group may have from 2 to 30 carbon atoms, alternatively from 2 to 24 carbon atoms, alternatively from 2 to 20 carbon atoms, alternatively from 2 to 12 carbon atoms, alternatively from 2 to 10 carbon atoms, alternatively from 2 to 6 carbon atoms. Alternatively, A) the polyorganosiloxane includes at least two silicon-bonded alkenyl groups per molecule and may be free from silicon-bonded alkynyl groups.

Alternatively, A) the polyorganosiloxane is substantially linear, alternatively is linear. In these embodiments, the substantially linear polyorganosiloxane may have the average formula: $R^4_{a'} SiO_{(4-a')/2}$, where each $R^4$ and is as defined above, and where subscript a' is selected such that 1.9≤a'≤2.2.

In these embodiments, at RT, the substantially linear polyorganosiloxane may be a flowable liquid or may have the form of an uncured rubber. The substantially linear polyorganosiloxane may have a viscosity of 10 mPa·s to 30,000,000 mPa·s, alternatively 10 mPa·s to 10,000 mPa·s, alternatively 100 mPa·s to 1,000,000 mPa·s, and alternatively 100 mPa·s to 100,000 mPa·s at 25° C. Viscosity may be measured at RT via a Brookfield LV DV-E viscometer.

Alternatively, when A) the polyorganosiloxane is substantially linear or linear, the polyorganosiloxane may have the average formula: $(R^{4''}_3SiO_{1/2})_m(R^{4''}_2SiO_{2/2})_n(R^{4'}R^{4''}SiO_{2/2})_o$, where each $R^{4''}$ is a monovalent hydrocarbon group that is free of aliphatic unsaturation or a monovalent halogenated hydrocarbon group that is free of aliphatic unsaturation and each R4' is a monovalent hydrocarbon group having terminal aliphatic unsaturation or a monovalent halogenated hydrocarbon group having terminal aliphatic unsaturation, as defined above for $R^4$, and subscript m≥2, subscript n≥0, and subscript o≥2. Alternatively, m is 2 to 10, alternatively 2 to 8, and alternatively 2 to 6. Alternatively, subscript n is 0 to 1,000, alternatively 1 to 500, and alternatively 1 to 200. Alternatively, subscript o is 2 to 500, alternatively 2 to 200, and alternatively 2 to 100.

When A) the polyorganosiloxane is substantially linear, alternatively is linear, the at least two terminally aliphatically unsaturated groups may be bonded to silicon atoms in pendent positions, terminal positions, or in both pendent and terminal locations. As a specific example of the polyorganosiloxane having pendent silicon-bonded aliphatically unsaturated groups, starting material A) may have the average formula: $(CH_3)_3SiO[(CH_3)_2SiO]_n[(CH_3)ViSiO]_oSi(CH_3)_3$, where subscripts n and o are defined above, and Vi indicates a vinyl group. With regard to this average formula, any methyl group may be replaced with a different monovalent hydrocarbon group (such as alkyl or aryl), and any vinyl group may be replaced with a different terminally aliphatically unsaturated monovalent hydrocarbon group (such as allyl or hexenyl). Alternatively, as a specific example of A) the polyorganosiloxane having terminal silicon-bonded aliphatically unsaturated groups, starting material A) may have the average formula: $Vi(CH_3)_2SiO[(CH_3)_2SiO]_nSi(CH_3)_2Vi$, where subscript n and Vi are defined above. The dimethyl polysiloxane terminated with silicon-bonded vinyl groups may be used alone or in combination with the dimethyl, methyl-vinyl polysiloxane disclosed immediately above. With regard to this average formula, any methyl group may be replaced with a different monovalent hydrocarbon group, and any vinyl group may be replaced with any terminally aliphatically unsaturated monovalent hydrocarbon group. Because the at least two silicon-bonded aliphatically unsaturated groups may be both pendent and terminal, A) the polyorganosiloxane may alternatively have the average formula: $Vi(CH_3)_2SiO[(CH_3)_2SiO]_n[(CH_3)ViSiO]_oSiVi(CH_3)_2$, where subscripts n and o and Vi are defined above.

The substantially linear polyorganosiloxane can be exemplified by a dimethylpolysiloxane capped at both molecular terminals with dimethylvinylsiloxy groups, a methylphenylpolysiloxane capped at both molecular terminals with dimethylvinylsiloxy groups, a copolymer of a methylphenylsiloxane and dimethylsiloxane capped at both molecular terminals with dimethylvinylsiloxy groups, a copolymer of a methylvinylsiloxane and a methylphenylsiloxane capped at both molecular terminals with dimethylvinylsiloxy groups, a copolymer of a methylvinylsiloxane and diphenylsiloxane capped at both molecular terminals with dimethylvinylsiloxy groups, a copolymer of a methylvinylsiloxane, methylphenylsiloxane, and dimethylsiloxane capped at both molecular terminals with dimethylvinylsiloxy groups, a copolymer of a methylvinylsiloxane and a methylphenylsiloxane capped at both molecular terminals with trimethylsiloxy groups, a copolymer of a methylvinylsiloxane and diphenylsiloxane capped at both molecular terminals with trimethylsiloxy groups, and a copolymer of a methylvinylsiloxane, methylphenylsiloxane, and a dimethylsiloxane capped at both molecular terminals with trimethylsiloxy groups.

Alternatively, A) the polyorganosiloxane may be a resinous polyorganosiloxane. In these embodiments, the resinous polyorganosiloxane may have the average formula: $R^4_{a''}SiO_{(4-a'')/2}$, where each $R^4$ is as defined above, and where subscript a'' is selected such that 0.5≤a''≤1.7.

The resinous polyorganosiloxane has a branched or a three dimensional network molecular structure. At 25° C., the resinous polyorganosiloxane may be in a liquid or in a solid form. Alternatively, the resinous polyorganosiloxane may be exemplified by a polyorganosiloxane that comprises only T units, a polyorganosiloxane that comprises T units in combination with other siloxy units (e.g., M, D, and/or Q siloxy units), or a polyorganosiloxane comprising Q units in combination with other siloxy units (i.e., M, D, and/or T siloxy units). Typically, the resinous polyorganosiloxane comprises T and/or Q units. Specific example of the resinous polyorganosiloxane include a vinyl-terminated silsesquioxane and a vinyl terminated MDQ resin.

Alternatively, starting material A) may comprise (A-I) a branched siloxane, (A-II) a silsesquioxane or both (A-I) and (A-II). Starting materials (A-I) and (A-II) may be particularly useful when the composition will be used for release coating applications. Starting material A) may be a combination of the (A-I) branched siloxane and (A-II) the silsesquioxane. The combination may be a physical blend or mixture. The branched siloxane and the silsesquioxane are present in amounts relative to one another such that the amount of (A-I) the branched siloxane and the amount of (A-II) the silsesquioxane combined total 100 weight parts, based on the weight of the release coating composition. The branched siloxane may be present in an amount of 50 to 100 parts by weight, and the silsesquioxane may be present in an amount of 0 to 50 parts by weight. Alternatively, the branched siloxane may be present in an amount 50 to 90 parts by weight and the silsesquioxane may be present in an amount of 10 to 50 parts by weight. Alternatively, the branched siloxane may be present in an amount of 50 to 80 parts by weight and the silsesquioxane may be present in an amount of 20 to 50 parts by weight. Alternatively, the branched siloxane may be present in an amount of 50 to 76 parts by weight and the silsesquioxane may be present in an amount of 24 to 50 parts by weight. Alternatively, the branched siloxane may be present in an amount of 50 to 70 parts by weight and the silsesquioxane may be present in an amount of 30 to 50 parts by weight. Without wishing to be bound by theory, it is thought that if the amount of silsesquioxane (A-II) exceeds 50 weight parts, per 100 weight parts the combined amounts of (A-I) the branched siloxane and (A-II) the silsesquioxane, the release coating formed from the composition may suffer from the drawback of migration, where silsesquioxane can migrate and contaminate an adherend such as a pressure sensitive adhesive in contact with the release coating.

Starting material (A-I) the branched siloxane has unit formula (A-I): $(R^1_3SiO_{1/2})_p(R^2R^1_2SiO_{1/2})_q(R^1_2SiO_{2/2})_r(SiO_{4/2})_s$, where each $R^1$ is independently a monovalent hydrocarbon group free of aliphatic unsaturation or a monovalent halogenated hydrocarbon group free of aliphatic unsaturation and each $R^2$ is an aliphatically unsaturated monovalent hydrocarbon group, subscript p≥0, subscript q>0, 15≥r≥995, and subscript s is >0.

The monovalent hydrocarbon group for $R^1$ is exemplified by an alkyl group of 1 to 6 carbon atoms, an aryl group of 6 to 10 carbon atoms, a halogenated alkyl group of 1 to 6 carbon atoms, a halogenated aryl group of 6 to 10 carbon atoms, an aralkyl group of 7 to 12 carbon atoms or a halogenated aralkyl group of 7 to 12 carbon atoms. Suitable alkyl groups for $R^1$ are exemplified by, but not limited to, methyl, ethyl, propyl (e.g., iso-propyl and/or n-propyl), butyl (e.g., isobutyl, n-butyl, tert-butyl, and/or sec-butyl), pentyl (e.g., isopentyl, neopentyl, and/or tert-pentyl), hexyl, as well as branched saturated hydrocarbon groups of 6 carbon atoms. Suitable aryl groups for $R^1$ are exemplified by, but not limited to, phenyl, tolyl, xylyl, and naphthyl. Suitable aralkyl groups for $R^1$ are exemplified by benzyl and dimethyl phenyl. Suitable halogenated alkyl groups for $R^1$ are exemplified by, but not limited to, the alkyl groups described above where one or more hydrogen atoms is replaced with a halogen atom, such as F or Cl. For example, fluoromethyl, 2-fluoropropyl, 3,3,3-trifluoropropyl, 4,4,4-trifluorobutyl, 4,4,4,3,3-pentafluorobutyl, 5,5,5,4,4,3,3-heptafluoropentyl, 6,6,6,5,5,4,4,3,3-nonafluorohexyl, and 8,8,8,7,7-pentafluorooctyl, 2,2-difluorocyclopropyl, 2,3-difluorocyclobutyl, 3,4-difluorocyclohexyl, and 3,4-difluoro-5-methylcycloheptyl, chloromethyl, chloropropyl, 2-dichlorocyclopropyl, and 2,3-dichlorocyclopentyl are examples of suitable halogenated alkyl groups. Suitable halogenated aryl groups for $R^1$ are exemplified by, but not limited to, the aryl groups described above where one or more hydrogen atoms is replaced with a halogen atom, such as F or Cl. For example, chlorobenzyl and fluorobenzyl are suitable halogenated aryl groups. Alternatively, each $R^1$ is independently a monovalent hydrocarbon group free of aliphatic unsaturation. Alternatively, each $R^1$ is an alkyl group. Alternatively, each $R^1$ is independently methyl, ethyl or propyl. Each instance of $R^1$ may be the same or different. Alternatively, each $R^1$ is a methyl group.

The aliphatically unsaturated monovalent hydrocarbon group for $R^2$ is capable of undergoing hydrosilylation reaction. Suitable aliphatically unsaturated hydrocarbon groups for $R^2$ are exemplified by an alkenyl group as defined above and exemplified by vinyl, allyl, butenyl, and hexenyl; and alkynyl groups as defined above and exemplified by ethynyl and propynyl. Alternatively, each $R^2$ may be vinyl or hexenyl. Alternatively, each $R^2$ is a vinyl group. The subscripts in the unit formula for (A-I) above may have values sufficient that the alkenyl or alkynyl content of the branched siloxane for (A-I) may be 0.1% to 1%, alternatively 0.2% to 0.5%, based on the weight of branched siloxane (A-I).

In the unit formula for (A-I), subscript $p \geq 0$. Subscript $q > 0$. Alternatively, subscript $q \geq 3$. Subscript r is 15 to 995. Subscript s is >0. Alternatively, subscript $s \geq 1$. Alternatively, for subscript p: $22 \geq p \geq 0$; alternatively $20 \geq p \geq 0$; alternatively $15 \geq p \geq 0$; alternatively $10 \geq p \geq 0$; and alternatively $5 \geq p \geq 0$. Alternatively, for subscript q: 22 $q > 0$; alternatively $22 \geq q \geq 4$; alternatively $20 \geq q > 0$; alternatively $15 \geq q > 1$; alternatively $10 \geq q \geq 2$; and alternatively $15 \geq q \geq 4$. Alternatively, for subscript r: $800 \geq r \geq 15$; and alternatively $400 \geq r \geq 15$. Alternatively, for subscript s: $10 \geq s > 0$; alternatively $10 \geq s \geq 1$; alternatively $5 \geq s > 0$; and alternatively $s=1$. Alternatively, subscript s is 1 or 2. Alternatively, when subscript $s=1$, subscript p may be 0 and subscript q may be 4.

The branched siloxane may contain at least two polydiorganosiloxane chains of formula $(R^1_2SiO_{2/2})_t$, where each subscript t is independently 2 to 100. Alternatively, the branched siloxane may comprise at least one unit of formula $(SiO_{4/2})$ bonded to four polydiorganosiloxane chains of formula $(R^1_2SiO_{2/2})_u$, where each subscript u is independently 1 to 100. Suitable branched siloxanes for starting material (A-I) are exemplified by those disclosed in U.S. Pat. No. 6,806,339 and U.S. Patent Publication 2007/0289495.

The silsesquioxane has unit formula (A-II): $(R^1_3SiO_{1/2})_i$ $(R^2R^1_2SiO_{1/2})_f(R^1_2SiO_{2/2})_g(R^1SiO_{3/2})_h$, where $R^1$ and $R^2$ are as described above, subscript $i \geq 0$, subscript $f > 0$, subscript g is 15 to 995, and subscript $h > 0$. Subscript i may be 0 to 10. Alternatively, for subscript i: $12 \geq i \geq 0$; alternatively $10 \geq i \geq 0$; alternatively $7 \geq i \geq 0$; alternatively $5 \geq i \geq 0$; and alternatively $3 \geq i \geq 0$.

Alternatively, subscript $f \geq 1$. Alternatively, subscript $f \geq 3$. Alternatively, for subscript f: $12 \geq f > 0$; alternatively $12 \geq f \geq 3$; alternatively $10 \geq f > 0$; alternatively $7 \geq f > 1$; alternatively $5 \geq f \geq 2$; and alternatively $7 \geq f \geq 3$. Alternatively, for subscript g: $800 \geq g \geq 15$; and alternatively $400 \geq g \geq 15$. Alternatively, subscript $h \geq 1$. Alternatively, subscript h is 1 to 10. Alternatively, for subscript h: $10 \geq h > 0$; alternatively $5 \geq h > 0$; and alternatively $h=1$. Alternatively, subscript h is 1 to 10, alternatively subscript h is 1 or 2. Alternatively, when subscript $h=1$, then subscript f may be 3 and subscript i may be 0. The values for subscript f may be sufficient to provide the silsesquioxane of unit formula (AII) with an alkenyl content of 0.1% to 1%, alternatively 0.2% to 0.6%, based on the weight of the silsesquioxane. Suitable silsesquioxanes for starting material A) are exemplified by those disclosed in U.S. Pat. No. 4,374,967.

Starting material A) may comprise a combination or two or more different polyorganosiloxanes that differ in at least one property such as structure, molecular weight, monovalent groups bonded to silicon atoms and content of aliphatically unsaturated groups. The curable composition may contain 60% to 98%, alternatively 60% to 95% of starting material A), based on combined weights of all starting materials in the composition.

The curable composition further comprises B) a polyorganohydrogensiloxane having an average, per molecule, of at least 2 silicon bonded hydrogen atoms. The silicon-bonded hydrogen atoms may be terminal, pendent, or in both terminal and pendent locations in B) the polyorganohydrogensiloxane.

The polyorganohydrogensiloxane may comprise any combination of M, D, T and/or Q siloxy units, so long as the polyorganohydrogensiloxane includes at least two silicon-bonded hydrogen atoms. These siloxy units can be combined in various manners to form cyclic, linear, branched and/or resinous (three-dimensional networked) structures. The polyorganohydrogensiloxane may be polymeric, oligomeric, linear, branched, cyclic, resinous, or combinations of two or more thereof, depending on the selection of M, D, T, and/or Q units.

Because the polyorganohydrogensiloxane includes an average of at least two silicon-bonded hydrogen atoms per molecule, with reference to the siloxy units set forth above, the polyorganohydrogensiloxane may comprise any of the following siloxy units including silicon-bonded hydrogen atoms, optionally in combination with siloxy units which do not include any silicon-bonded hydrogen atoms: $(R^5_2HSiO_{1/2})$, $(R^5H_2SiO_{1/2})$, $(H_3SiO_{1/2})$, $(R^5HSiO_{2/2})$, $(H_2SiO_{2/2})$, and/or $(HSiO_{3/2})$, where each $R^5$ is independently a monovalent hydrocarbon group or a monovalent halogenated hydrocarbon group.

Each $R^5$ is an independently selected monovalent hydrocarbon group or monovalent halogenated hydrocarbon group, as introduced above, and may be linear, branched, cyclic, or combinations thereof. Cyclic hydrocarbon groups encompass aryl groups as well as saturated or non-conjugated cyclic groups. Aryl groups may be monocyclic or polycyclic. Linear and branched hydrocarbon groups may independently be saturated or unsaturated. One example of a combination of a linear and cyclic hydrocarbon group is an aralkyl group. Suitable monovalent hydrocarbon groups may be exemplified by alkyl, alkenyl groups, alkynyl groups, aryl groups, and aralkyl groups, as described above for $R^4$. Suitable monovalent halogenated hydrocarbon groups are also as described above for $R^4$. Alternatively, each $R^5$ may be an independently selected monovalent hydrocarbon group.

Alternatively, the polyorganohydrogensiloxane may have the average formula: $(R^6{}_3SiO_{1/2})_{hh}(R^5{}_2SiO_{2/2})_{ii}(R^5HSiO_{2/2})_{jj}$, where each $R^6$ is independently hydrogen or $R^5$, each $R^5$ is as described above, and subscript hh≥2, subscript ii≥0, and subscript jj≥2. Alternatively, subscript hh is 2 to 10, alternatively 2 to 8, and alternatively 2 to 6. Alternatively, subscript ii is 0 to 1,000, alternatively 1 to 500, and alternatively 1 to 200. Alternatively, subscript jj is 2 to 500, alternatively 2 to 200, and alternatively 2 to 100. Alternatively, each $R^6$ is $R^5$.

Alternatively, the polyorganohydrogensiloxane may have an average formula selected from: $(R^6{}_3SiO_{1/2})_{hh}(R^5{}_2SiO_{2/2})_{ii}(R^5HSiO_{2/2})_{jj}(R^5SiO_{3/2})_{kk}$, $(R^6{}_3SiO_{1/2})_{hh}(R^5{}_2SiO_{2/2})_{ii}(R^5HSiO_{2/2})_{jj}(SiO_{4/2})_{mm}$, $(R^6{}_3SiO_{1/2})_{hh}(R^5{}_2SiO_{2/2})_{ii}(R^5HSiO_{2/2})_{jj}(SiO_{4/2})_{mm}(R^5SiO_{3/2})_{kk}$, and combinations of two or more thereof; where each $R^6$, $R^5$, and subscripts hh, ii, and jj are as defined above, subscript kk≥0, and subscript mm is ≥0. In each of the average formulas above, the sum of the subscripts is 1.

Alternatively, the poly organohydrogensiloxane is linear and includes pendent silicon-bonded hydrogen atoms. This polyorganohydrogensiloxane may be a dimethyl, methyl-hydrogen polysiloxane having the average formula:

$(CH_3)_3SiO[(CH_3)_2SiO]_{ii}[(CH_3)HSiO]_{jj}Si(CH_3)_3$ where subscripts ii and jj are defined above.

Alternatively, B) the polyorganohydrogensiloxane is linear and includes terminal silicon-bonded hydrogen atoms. This polyorganohydrogensiloxane may be an SiH terminal dimethyl polysiloxane having the average formula:

$H(CH_3)_2SiO[(CH_3)_2SiO]_{ii}Si(CH_3)_2H$ where subscript ii is as defined above. The SiH terminal dimethyl polysiloxane may be used alone or in combination with the dimethyl, methyl-hydrogen polysiloxane disclosed immediately above. When a mixture is used, the relative amount of each organohydrogensiloxane in the mixture may vary.

Alternatively still, the polyorganohydrogensiloxane may include both pendent and terminal silicon-bonded hydrogen atoms. In certain embodiments, the polyorganohydrogensiloxane may comprise an alkylhydrogen cyclosiloxane or an alkylhydrogen dialkyl cyclosiloxane copolymer, represented in general by the formula $(R^6{}_2SiO)_{nn}(R^5HSiO)_{oo}$, where $R^6$ and $R^5$ are as defined above, and where subscript nn is an integer from 0 to 7 and subscript oo is an integer from 3 to 10. Specific examples of suitable organohydrogensiloxanes of this type include $(OSiMeH)_4$, $(OSiMeH)_3(OSiMeC_6H_{13})$, $(OSiMeH)_2(OSiMeC_6H_{13})_2$, and $(OSiMeH)(OSiMeC_6H_{13})_3$, where Me represents methyl ($—CH_3$).

Other examples of suitable polyorganohydrogensiloxanes are those having at least two SiH containing cyclosiloxane rings in one molecule. Such an organohydrogensiloxane may be any organopolysiloxane having at least two cyclosiloxane rings with at least one silicon-bonded hydrogen (SiH) atom on each siloxane ring. Cyclosiloxane rings contain at least three siloxy units (that is the minimum needed to form a siloxane ring), and may be any combination of M, D, T, and/or Q siloxy units that forms a cyclic structure, provided that at least one of the cyclic siloxy units on each siloxane ring contains one SiH unit, which may be an M siloxy unit, a D siloxy unit, and/or a T siloxy unit. These siloxy units can be represented as MH, DH, and TH siloxy units respectively when other substituents are methyl.

Alternatively, starting material B) may be a crosslinker having an average of at least 3 silicon bonded hydrogen atoms per molecule, and the curable composition may be a release coating composition. The crosslinker may be present in the release coating composition in an amount sufficient to provide a molar ratio of silicon bonded hydrogen atoms to aliphatically unsaturated groups (SiH:Vi ratio) of >1:1 to 5:1, alternatively 1.2:1 to 2:1. The crosslinker may by a polyorganohydrogensiloxane crosslinker of unit formula (B-I): $(R^5{}_3SiO_{1/2})_2(R^5{}_2SiO_{2/2})_{pp}(R^5HSiO_{2/2})_{qq}$, where $R^5$ is as described above and subscript pp≥0, subscript qq>0, and a quantity (pp+qq) is 8 to 400. Subscripts pp and qq may have values selected such that the polyorganohydrogensiloxane crosslinker has a viscosity of from 5 to 1000 mPa·s at 25° C., alternatively 10 to 350 mPa·s.

Polyorganohydrogensiloxanes for starting material B) are exemplified by:

a) trimethylsiloxy-terminated poly(dimethylsiloxane/methylhydrogensiloxane), b) trimethylsiloxy-terminated polymethylhydrogensiloxane, and c) a combination of a) and b). The crosslinker may be one polyorganohydrogensiloxane crosslinker or a combination of two or more crosslinkers that differ in one or more properties selected from molecular weight, structure, siloxane units and sequence.

Alternatively, starting material B) in the curable composition (whether or not it is a release coating composition) may comprise a clustered functional polyorganohydrogensiloxane. The clustered functional polyorganohydrogensiloxane has unit formula: $(R^5{}_2HSiO_{1/2})_{aa}(R^5HSiO_{2/2})_{bb}(R^5{}_2SiO_{2/2})_{cc}(R^5SiO_{3/2})_{dd}(SiO_{4/2})_{ee}((R^5{}_{ff})O_{(3-ff)/2}SiD^1SiR^5{}_{ff}O_{(3-ff)/2})_{gg}$.

In this unit formula, $R^5$ is as described above, and each $D^1$ independently represents a divalent hydrocarbon group of 2 to 18 carbon atoms. Suitable divalent hydrocarbon groups for $D^1$ are exemplified by alkylene groups such as ethylene, propylene (including isopropylene and n-propylene), and butylene (including n-butylene, t-butylene and isobutylene); and pentylene, hexylene, heptylene, octylene, and branched and linear isomers thereof; arylene groups such as phenylene, e.g., ortho-phenylene; and alkaralkylene groups such as:

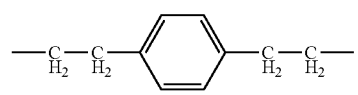

or

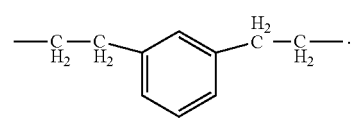

Alternatively, each divalent hydrocarbon group may be ethylene, propylene, butylene or hexylene. Alternatively, each divalent hydrocarbon group may be ethylene or propylene.

In the unit formula above, subscript aa≥0, subscript bb≥0, a quantity (aa+bb)≥4, subscript cc>0, subscript dd≥0, subscript ee≥0, subscript ff is 0, 1, or 2, subscript gg≥2. Alternatively, the quantity (aa+bb) may be ≥6. Alternatively, the quantity (aa+bb) may be ≥8. By the term "clustered functional polyorganohydrogensiloxane", it is meant that this compound has a linear or branched siloxane backbone structure and in the terminal and/or pendent positions of the clustered functional polyorganohydrogensiloxane there are silicon bonded hydrogen atoms spatially close to each other. The clustered functional polyorganohydrogensiloxane may have at least 4 total silicon bonded hydrogen atoms per molecule and at least two of them are in close proximity to each other, i.e., they are "clustered".

Alternatively, the clustered functional polyorganohydrogensiloxane may have formula:

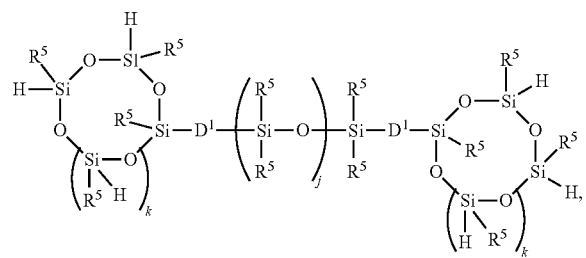

where $R^5$ and $D^1$ are as described above. Subscript j is 0 to 2,000,000, and each subscript k is independently 1 to 12 (i.e., such that each ring has 4 to 15 silicon atoms). Alternatively, subscript j is 5 to 500,000, alternatively 5 to 100,000, alternatively 5 to 50,000, alternatively 10 to 50,000, alternatively 10 to 10,000, alternatively 10 to 5,000, alternatively 20 to 2,000. Alternatively subscript k is 1 to 8, alternatively 1 to 6, alternatively 1 to 4, alternatively 1 to 2, and alternatively, k=1. Alternatively, B) the clustered functional polyorganohydrogensiloxane may have formula:

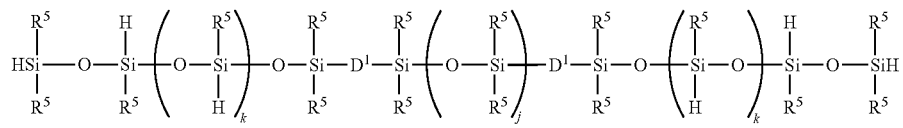

where $R^5$, $D^1$, and subscripts j and k are as described above.

The clustered functional polyorganohydrogensiloxane used herein may be a hydrosilylation reaction product of starting materials comprising:

a) a polyorganosiloxane having an average of at least two silicon bonded aliphatically unsaturated groups per molecule; and b) an organohydrogensiloxane having an average of 4 to 15 silicon atoms per molecule, where starting material b) has silicon bonded hydrogen atoms;

with the proviso that a molar ratio of aliphatically unsaturated groups in starting material a) to silicon bonded hydrogen atoms in starting material b) is 1 to 3 to 1 to 20. Clustered functional polyorganohydrogensiloxanes and method for their preparation are disclosed in U.S. Patent Application Publication 2016/0009865; U.S. Pat. Nos. 7,378,482; 7,429,636; 7,432,338; 7,449,536; and 7,906,605.

Starting material B) may comprise a combination or two or more different polyorganohydrogensiloxanes that differ in at least one property such as structure, molecular weight, monovalent groups bonded to silicon atoms and SiH content.

The curable composition may comprise starting materials A) and B) in varying amounts or ratios contingent on desired properties or end use application of the curable composition. In various embodiments, the curable composition comprises starting materials A) and B) in an amount to provide a mole ratio of silicon-bonded hydrogen atoms in starting material B) to aliphatically unsaturated groups in starting material A) of 0.3 to 5, alternatively 0.6 to 3. The amount of starting material B) added to the release coating composition may be 0.5 to 20 parts by weight per 100 parts by weight of starting material A).

The curable composition further comprises starting material C) a hydrosilylation-reaction catalyst. The hydrosilylation-reaction catalyst is not limited and may be any known hydrosilylation-reaction catalyst for catalyzing hydrosilylation reactions. One single hydrosilylation-reaction catalyst may be used, or combinations of two or more different hydrosilylation-reaction catalysts may be used.

The C) hydrosilylation-reaction catalyst may comprise a metal selected from platinum, rhodium, ruthenium, palladium, osmium, and iridium; alternatively platinum. Alternatively, the C) hydrosilylation-reaction catalyst may be a compound of the metal, exemplified by, for example, platinum compounds such as chloroplatinic acid, chloroplatinic acid hexahydrate, or platinum dichloride. Alternatively, the C) hydrosilylation reaction catalyst may be a reaction product of the compound, such as a reaction product of chloroplatinic acid and a monohydric alcohol, platinum bis(ethylacetoacetate), platinum bis(acetylacetonate), platinum chloride. Alternatively, the C) hydrosilylation reaction catalyst may comprise a complex of the compound with an olefin or an organopolysiloxane. Complexes of platinum with low molecular weight organopolysiloxanes include 1,3-diethenyl-1,1,3,3-tetramethyldisiloxane complexes with platinum. Exemplary hydrosilylation catalysts are described in U.S. Pat. Nos. 3,159,601; 3,220,972; 3,296,291; 3,419,593; 3,516,946; 3,814,730; 3,989,668; 4,784,879; 5,036,117; and 5,175,325 and EP 0 347 895 B. Alternatively, C) the hydrosilylation reaction catalyst may be a compound or complex described above, such as a platinum compound, microencapsulated in a resin matrix or core-shell type structure. Microencapsulated hydrosilylation catalysts and methods of their preparation are also known in the art, as exemplified in U.S. Pat. Nos. 4,766,176 and 5,017,654, which are incorporated by reference herein in their entireties.

The C) hydrosilylation-reaction catalyst is present in the curable composition in a catalytic amount, i.e., an amount or quantity sufficient to promote curing thereof at desired conditions. The catalytic amount of the C) hydrosilylation-reaction catalyst may be greater than 0.01 ppm, and may be greater than 1,000 ppm (e.g., up to 10,000 ppm or more). In certain embodiments, the typical catalytic amount of C) hydrosilylation-reaction catalyst is less than 5,000 ppm, alternatively less than 2,000 ppm, alternatively less than 1,000 ppm (but in any case greater than 0 ppm). In specific embodiments, the catalytic amount of the C) hydrosilylation-reaction catalyst may range from 0.01 to 1,000 ppm, alternatively 0.01 ppm to 100 ppm, alternatively 20 ppm to 200 ppm, and alternatively 0.01 to 50 ppm of platinum group metal based on combined weights of all starting materials in the curable composition.

The curable composition further comprises starting material D), a 2-substituted-1-alknyl-1-cyclohexanol. The 2-substituted-1-alknyl-1-cyclohexanol may have the general formula

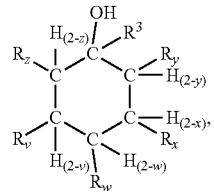

where $R^3$ is an alkynyl group having at least 2 carbon atoms, each R is independently a monovalent hydrocarbon group having at least 1 carbon atom, subscript v is 0 to 2, subscript w is 0 to 2, subscript x is 0 to 2, subscript y is 0 to 2, subscript z is 0 to 2, with the provisos that a quantity (v+w+x+y+z)>1, and a quantity (y+z) is 1 to 4. Alternatively, (y+z) is 1 to 2. Alternatively, (v+w+x+y+z) is 1 to 4. Alternatively, (v+w+x+y+z) is 1 to 3. Alternatively, (v+w+x+y+z) is 1 to 2. Alternatively, (v+w+x+y+z) is 2. Alternatively, in one embodiment (y+z)=2 and a quantity (v+w+x)=0. In this embodiment, the structure is both 2-substituted and 6-substituted. In an alternative embodiment (y+z)=1 and (v+w+x)=1. In this embodiment, either y can be 1 or z can be 1 and the structure will be 2-substituted. Suitable monovalent hydrocarbon groups are exemplified by alkyl, alkenyl groups, alkynyl groups, aryl groups, and aralkyl groups, as described above for $R^5$. Suitable alkynyl groups are exemplified by, but not limited to, ethynyl, propynyl, and butynyl. The alkynyl group may have from 2 to 30 carbon atoms, alternatively from 2 to 24 carbon atoms, alternatively from 2 to 20 carbon atoms, alternatively from 2 to 12 carbon atoms, alternatively from 2 to 10 carbon atoms, alternatively from 2 to 6 carbon atoms. Alternatively, each R may be an alkyl group of 1 to 20 carbon atoms or an aryl group of 6 to 20 carbon atoms, and each $R^3$ may be an alkynyl group of 2 to 6 carbon atoms. Alternatively, each R may be methyl or isopropyl and each $R^3$ may be ethynyl. Alternatively, in one embodiment, the 2-substituted-1-alkynyl-1-cyclohexanol of the formula above may have subscript w=1, subscript z=1, and subscripts v=x=y=0. In this embodiment, the 2-substituted-1-alkynyl-1-cyclohexanol may have general formula (D-I):

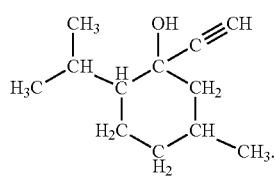

In an alternative embodiment, the 2-substituted-1-alkynyl-1-cyclohexanol may have subscript z=2 and subscripts v=w=x=y=0. In this embodiment, the 2-substituted-1-alkynyl-1-cyclohexanol may have general formula (D-II):

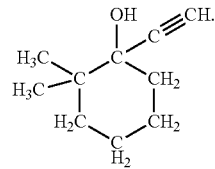

The 2-substituted-1-alkynyl-1-cyclohexanol may be prepared by a method comprising:
(1) combining starting materials comprising
   (a) a substituted cyclohexanone compound, and
   (b) a reagent of formula $R^3MX_{rr}$, where $R^3$ is the alkynyl group of at least two carbon atoms (as described above), M is a metal atom selected from Mg or Li, X is a halogen atom selected from Br, Cl, and I, and subscript rr is 0 or 1, depending on the selection of M (e.g., when M is magnesium (Mg), subscript rr is 1; when M is lithium (Li), subscript rr is 0). Starting material (a) may be a commercially available compound, such as (−)-Menthone or 2,2-dimethylcyclohexanone. Starting material (b) may be a commercially available compound, such as ethynyl magnesium bromide or lithium acetylide.

The method for preparing the 2-substituted-1-alkynyl-1-cyclohexanol may further comprise: (2) quenching the product of step (1) by adding aqueous $NH_4X^1$, where $X^1$ represents a halogen atom, which may be the same as or different from the halogen atom selected for X; and/or (3) recovering the 2-substituted-1-alkynyl-1-cyclohexanol, which may be performed by any conventional means such as stripping, distillation, flash chromatography on silica gel, and combinations thereof.

Alternatively, the 2-substituted-1-alkynyl-1-cyclohexanol may be prepared by a method comprising: 1) combining starting materials comprising (a) the substituted cyclohexanone compound described above and (c) a lithium alkynyl diamine complex, such as lithium acetylide ethylenediamine complex. A solvent may optionally be added to the starting materials in step 1). This method may further comprise steps (2) and (3) as described above. Without wishing to be bound by theory, it is thought that one skilled in the art would be able to prepare the 2-substituted-1-alkynyl-1-cyclohexanol as described in the examples herein by varying the starting materials and selecting appropriate process conditions as disclosed in "SUPPORTING INFORMATION, 11-Step Total Synthesis of (−)-Maoecrystal V," by Artiom Cernijenko, Rune Risgaard, and Phil S. Baran, Department of Chemistry, The Scripps Research Institute, 10550 North Torrey Pines Road, La Jolla, Calif. 92037 and "Hydromethylation of Unactivated Olefins," by Hai T. Dao, Chao Li, Quentin Michaudel, Brad D. Maxwell, and Phil S. Baran, Journal of the American Chemical Society, May 18, 2015, DOI: 10.1021/jacs.5b05144.

The 2-substituted-1-alkynyl-1-cyclohexanol is useful as an inhibitor in hydrosilylation reaction curable compositions, such as release coating compositions. The amount of the 2-substituted-1-alkynyl-1-cyclohexanol added to the curable composition will depend on various factors including the desired bulk bath life of the composition, whether the curable composition will be a one part composition or a multiple part composition, the particular species of starting material D) used, and the selection and amount of starting material B). However, the amount of the 2-substituted-1- alkynyl-1-cyclohexanol may be 0.001 to 1 parts by weight of inhibitor per 100 parts by weight of starting material A). Alternatively, the amount of inhibitor may be alternatively 0.001% to 5%, alternatively 0.0025% to 3%, alternatively 0.005% to 0.6%, alternatively 0.001% to 1%, alternatively 0.01% to 0.5%, and alternatively 0.0025% to 0.025%, based on combined weights of all starting materials in the curable composition.

The curable composition may further comprise one or more optional components, including adhesion promoters, carrier vehicles, dyes, pigments, anti-oxidants, heat stabilizers, flame retardants, flow control additives, biocides, fillers (including extending and reinforcing fillers), surfactants, thixotroping agents, water, carrier vehicles or solvents, and pH buffers. The curable composition may be in any form and may be incorporated into further compositions, e.g. as a component of a composition. For example, the curable composition may be in the form of, or incorporated into, an emulsion. The emulsion may be an oil-in-water emulsion, water-in-oil emulsion, or silicone-in-oil emulsion. The curable composition itself may be a continuous or discontinuous phase of such an emulsion.

Suitable carrier vehicles include silicones, both linear and cyclic, organic oils, organic solvents and mixtures of these. Specific examples of solvents may be found in U.S. Pat. No. 6,200,581, which is hereby incorporated by reference for this purpose.

Typically, the carrier vehicle, if present, is an organic liquid. Organic liquids includes those considered oils or solvents. The organic liquids are exemplified by, but not limited to, aromatic hydrocarbons, aliphatic hydrocarbons, alcohols having more than 3 carbon atoms, aldehydes, ketones, amines, esters, ethers, glycols, glycol ethers, alkyl halides and aromatic halides. Hydrocarbons include, isododecane, isohexadecane, Isopar L (C11-C13), Isopar H(C11-C12), hydrogenated polydecene. Ethers and esters include, isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, octyl ether, and octyl palmitate. Additional organic carrier fluids suitable as a stand-alone compound or as an ingredient to the carrier fluid include fats, oils, fatty acids, and fatty alcohols. The carrier vehicle may also be a low viscosity organopolysiloxane or a volatile methyl siloxane or a volatile ethyl siloxane or a volatile methyl ethyl siloxane having a viscosity at 25° C. in the range of 1 to 1,000 mm$^2$/sec, such as hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, hexamethyl-3,3, bis{(trimethylsilyl)oxy}trisiloxane pentamethyl{(trimethylsilyl)oxy}cyclotrisiloxane as well as polydimethylsiloxanes, polyethylsiloxanes, polymethylethylsiloxanes, polymethylphenylsiloxanes, polydiphenylsiloxanes, caprylyl methicone, and any mixtures thereof.

When the curable composition will be used as a release coating composition, the release coating composition may optionally further comprise one or more additional starting materials selected from: E) a polydiorganosiloxane having an average, per molecule, of one or groups with terminal aliphatic unsaturation, which is distinct from starting material A), F) an anchorage additive, G) a solvent, H) an anti-mist additive, I) a controlled release agent, and J) a colorant.

Starting material E) is a polydiorganosiloxane having an average of one or more terminally aliphatically unsaturated groups per molecule. Starting material E) may comprise a polydiorganosiloxane of $$(R^1_2R^2SiO_{1/2})_2(R^1_2SiO)_{ss}(R^1R^2SiO)_{tt},\quad \text{Unit Formula (E-I):}$$

$$(R^1_3SiO_{1/2})_2(R^1_2SiO)_{uu}(R^1R^2SiO)_{vv},\quad \text{Unit Formula (E-II):}$$

or a combination thereof.

In unit formulae (E-I) and (E-II), $R^1$ is a monovalent hydrocarbon group free of aliphatic unsaturation and $R^2$ is an aliphatically unsaturated monovalent hydrocarbon group as described above. Subscript ss is 5 to 10,000. Subscript tt has a value sufficient to provide an $R^2$ content of 0.05% to 0.90% based on weight of the polydiorganosiloxane of unit formula (E-I). Subscript uu is 5 to 10,000. Subscript vv is sufficient to provide an $R^2$ content of 0.05% to 0.90% based on weight of the polydiorganosiloxane of unit formula (E-II).

Starting material E) may comprise a polydiorganosiloxane such as
i) dimethylvinylsiloxy-terminated polydimethylsiloxane,
ii) dimethylvinylsiloxy-terminated poly(dimethylsiloxane/methylvinylsiloxane),
iii) dimethylvinylsiloxy-terminated polymethylvinylsiloxane,
iv) trimethylsiloxy-terminated poly(dimethylsiloxane/methylvinylsiloxane),
v) trimethylsiloxy-terminated polymethylvinylsiloxane,
vi) dimethylvinylsiloxy-terminated poly(dimethylsiloxane/methylvinylsiloxane),
vii) dimethylvinylsiloxy-terminated poly(dimethylsiloxane/methylphenylsiloxane),
viii) dimethylvinylsiloxy-terminated poly(dimethylsiloxane/diphenylsiloxane),
ix) phenyl,methyl,vinyl-siloxy-terminated polydimethylsiloxane,
x) dimethylhexenylsiloxy-terminated polydimethylsiloxane,
xi) dimethylhexenylsiloxy-terminated poly(dimethylsiloxane/methylhexenylsiloxane),
xii) dimethylhexenylsiloxy-terminated polymethylhexenylsiloxane,
xiii) trimethylsiloxy-terminated poly(dimethylsiloxane/methylhexenylsiloxane),
xiv) trimethylsiloxy-terminated polymethylhexenylsiloxane
xv) dimethylhexenyl-siloxy terminated poly(dimethylsiloxane/methylhexenylsiloxane),
xvi) dimethylvinylsiloxy-terminated poly(dimethylsiloxane/methylhexenylsiloxane)
xvii) a combination thereof.

The amount of starting material E) added to the release coating composition will depend on various factors including the type and amount the polyorganohydrogensiloxane selected for starting material B), the silicon bonded hydrogen content of starting material B), and the aliphatic unsaturation content of starting material A). However, starting material E) may be added to the release coating composition in an amount of 0 to 50 parts by weight per 100 parts by weight of starting material A). Alternatively, starting material E) may be added to the release coating composition in an amount of 5 to 25 parts by weight. Starting material E)

may be one polydiorganosiloxane or a combination of more than one polydiorganosiloxane that differ in one or more properties selected from molecular weight, structure, siloxane units and sequence.

Starting material F) is an anchorage additive. Suitable anchorage additives are exemplified by a reaction product of a vinyl alkoxysilane and an epoxy-functional alkoxysilane; a reaction product of a vinyl acetoxysilane and epoxy-functional alkoxysilane; and a combination (e.g., physical blend and/or a reaction product) of a polyorganosiloxane having at least one aliphatically unsaturated hydrocarbon group and at least one hydrolyzable group per molecule and an epoxy-functional alkoxysilane (e.g., a combination of a hydroxy-terminated, vinyl functional polydimethylsiloxane with glycidoxypropyltrimethoxysilane). Suitable anchorage additives and methods for their preparation are disclosed, for example, in U.S. Pat. No. 9,562,149; U.S. Patent Application Publication Numbers 2003/0088042, 2004/0254274, and 2005/0038188; and European Patent 0 556 023. The exact amount of anchorage additive depends on various factors including the type of substrate and whether a primer is used, however, the amount of anchorage additive in the release coating composition may be 0 to 2 parts by weight, per 100 parts by weight of starting material A). Alternatively, the amount of anchorage additive, may be 0.01 to 2 parts by weight, per 100 parts by weight of starting material A).

Starting material G) is a solvent. Suitable solvents include the carrier vehicles described above. Alternatively, the solvent may be selected from polyalkylsiloxanes, alcohols, ketones, aromatic hydrocarbons, aliphatic hydrocarbons, glycol ethers, tetrahydrofuran, mineral spirits, naphtha, tetrahydrofuran, mineral spirits, naphtha, or a combination thereof. Polyalkylsiloxanes with suitable vapor pressures may be used as the solvent, and these include hexamethyldisiloxane, octamethyltrisiloxane, hexamethylcyclotrisiloxane and other low molecular weight polyalkylsiloxanes, such as 0.5 to 1.5 cSt Dow Corning® 200 Fluids and Dow Corning® OS FLUIDS, which are commercially available from Dow Corning Corporation of Midland, Mich., U.S.A.

Alternatively, starting material G) may comprise an organic solvent. The organic solvent can be an alcohol such as methanol, ethanol, isopropanol, butanol, or n-propanol; a ketone such as acetone, methylethyl ketone, or methyl isobutyl ketone; an aromatic hydrocarbon such as benzene, toluene, or xylene; an aliphatic hydrocarbon such as heptane, hexane, or octane; a glycol ether such as propylene glycol methyl ether, dipropylene glycol methyl ether, propylene glycol n-butyl ether, propylene glycol n-propyl ether, or ethylene glycol n-butyl ether, tetrahydrofuran; mineral spirits; naphtha; or a combination thereof.

The amount of solvent will depend on various factors including the type of solvent selected and the amount and type of other starting materials selected for the release coating composition. However, the amount of solvent may be 0% to 99%, alternatively 2% to 50%, based on the weight of all starting materials in the release coating composition. The solvent may be added during preparation of the release coating composition, for example, to aid mixing and delivery. All or a portion of the solvent may optionally be removed after the release coating composition is prepared.

Starting material H) is an anti-mist additive that may be added to the release coating composition to reduce or suppress silicone mist formation in coating processes, particularly with high speed coating equipment. The anti-mist additive may be a reaction product of an organohydrogensilicon compound, an oxyalkylene compound or an organoalkenylsiloxane with at least three silicon bonded alkenyl groups per molecule, and a suitable catalyst. Suitable anti-mist additives for starting material H) are disclosed, for example, in U.S. Patent Application 2011/0287267; U.S. Pat. Nos. 8,722,153; 6,586,535; and 5,625,023.

The amount of anti-mist additive will depend on various factors including the amount and type of other starting materials selected for the release coating composition. However, the amount of anti-mist additive may be 0% to 10%, alternatively 0.1% to 3%, based on the weight of all starting materials in the release coating composition.

The release coating composition may contain a release modifier to control (decrease) the level of release force (the adhesive force between the release coating and an adherend thereto, such as a label including a pressure sensitive adhesive). Release coating compositions having the required release force can be formulated from a modifier-free release coating composition by adjusting the level of modifier. Examples of suitable release modifiers include trimethylsiloxy-terminated dimethyl, phenylmethylsiloxanes. Alternatively, the release modifier may be a condensation reaction product of an organopolysiloxane resin having hydroxyl or alkoxy groups and a diorganopolysiloxane with at least one hydroxyl or hydrolyzable group. If used, a release modifier can, for example, be used at 0 to 85 parts by weight, alternatively 25 to 85 parts, per 100 parts of starting material A). Examples of suitable release modifiers are disclosed, for example, in U.S. Pat. No. 8,933,177 and U.S. Patent Application Publication 2016/0053056.

Other optional starting materials which may also be added to release coating compositions described herein include, for example, reactive diluents, fragrances, preservatives and fillers, for example, silica, quartz or chalk.

When selecting starting materials for the release coating composition (and other curable compositions described herein), there may be overlap between types of starting materials because certain starting materials described herein may have more than one function. Certain particulates may be useful as fillers and as pigments, and even as flame retardants, e.g., carbon black. When adding additional starting materials to the composition, the additional starting materials are distinct from starting materials A) to D) and from one another.

Alternatively, the release coating may be free of filler or contains only a limited amount of filler, such as 0 to 30% by weight of the release coating composition. Fillers can agglomerate or otherwise stick to the coater equipment used to apply the release coating. They can hinder optical properties, for example transparency, of the release coating and of the release liner formed therewith, if optical transparency is desired. The fillers may be prejudicial to the adherence of the adherend.

In one embodiment, the release coating composition of the invention may be free from fluoroorganosilicone compounds. It is believed that, during the cure, a fluorocompound, because of its low surface tension, will rapidly migrate to the interface of a coating composition and a substrate, for example a polyorganosiloxane release coating composition/PET film interface, and prevent adherence of the release coating (prepared by curing the release coating composition) to the substrate by making a fluorine containing barrier. By making a barrier, the fluorocompound prevents any component from reacting at the interface. Moreover, fluorosilicone compounds are usually expensive.

The curable composition may be prepared by combining starting materials comprising A), B), C) and D), along with any optional additional starting materials, in any order of addition, optionally with a master batch, and optionally under shear.

The present invention also provides a process of preparing a coated substrate with the curable composition. The method comprises disposing the curable composition on the substrate. The method further comprises curing the curable composition on the substrate. Curing may be performed by heating at an elevated temperature, e.g., 50° C. to 180° C., alternatively 50° C. to 120° C., and alternatively 50° C. to 90° C. to give the coated substrate. One skilled in the art would be able to select an appropriate temperature depending on various factors including the selection of optional starting materials in the curable composition and the substrate material of construction.

The curable composition may be disposed or dispensed on the substrate in any suitable manner. Typically, the curable composition is applied in wet form via a wet coating technique. In certain embodiments, the curable composition is applied by i) spin coating; ii) brush coating; iii) drop coating; iv) spray coating; v) dip coating; vi) roll coating; vii) flow coating; viii) slot coating; ix) gravure coating; x) Meyer bar coating; or xi) a combination of any of i) to x). Typically, disposing the curable composition on the substrate results in a wet deposit on the substrate, which is subsequently cured to give the coated substrate, which comprises a cured film formed from the curable composition on the substrate.

The substrate is not limited and may be any substrate. The cured film may be separable from the substrate or may be physically and/or chemically bonded to the substrate depending on its selection. The substrate may have an integrated hot plate or an integrated or stand-alone furnace for curing the deposit. The substrate may optionally have a continuous or non-continuous shape, size, dimension, surface roughness, and other characteristics. In certain embodiments, the substrate has a softening point temperature at the elevated temperature. However, the curable composition and method are not so limited.

In certain embodiments, the substrate comprises a plastic, which maybe a thermosetting and/or thermoplastic. However, the substrate may alternatively be glass, metal, paper, wood, cardboard, paperboard, a silicone, or polymeric materials, or a combination thereof.

Specific examples of suitable substrates include paper substrates such as Kraft paper, polyethylene coated Kraft paper (PEK coated paper), and regular papers; polymeric substrates such polyamides (PA); polyesters such as polyethylene terephthalates (PET), polybutylene terephthalates (PET), polytrimethylene terephthalates (PTT), polyethylene naphthalates (PEN), liquid crystalline polyesters, and the like; polyolefins such as polyethylenes (PE), polypropylenes (PP), polybutylenes, and the like; styrenic resins; polyoxymethylenes (POM); polycarbonates (PC); polymethylenemethacrylates (PMMA); polyvinyl chlorides (PVC); polyphenylene sulfides (PPS); polyphenylene ethers (PPE); polyimides (PI); polyamideimides (PAI); polyetherimides (PEI); polysulfones (PSU); polyethersulfones; polyketones (PK); polyetherketones; polyvinyl alcohols (PVA); polyetheretherketones (PEEK); polyetherketoneketones (PEKK); polyarylates (PAR); polyethernitriles (PEN); phenolic resins; phenoxy resins; celluloses such as triacetylcellulose, diacetylcellulose, and cellophane; fluorinated resins, such as polytetrafluoroethylenes; thermoplastic elastomers, such as polystyrene types, polyolefin types, polyurethane types, polyester types, polyamide types, polybutadiene types, polyisoprene types, and fluoro types; and copolymers, modifications, and combinations thereof.

The curable composition, or wet deposit, is typically cured at the elevated temperature for a period of time. The period of time is typically sufficient to effect curing, i.e., cross-linking, of the curable composition. In certain embodiments, the period of time is from greater than 0 to 8 hours, alternatively from greater than 0 to 2 hours, alternatively from greater than 0 to 1 hour, alternatively from greater than 0 to 30 minutes, alternatively from greater than 0 to 15 minutes, alternatively from greater than 0 to 10 minutes, alternatively from greater than 0 to 5 minutes, alternatively from greater than 0 to 2 minutes. The period of time depends on various factors including on the elevated temperature is utilized, the temperature selected, desired film thickness, and the presence of absence of any water or carrier vehicle in the curable composition.

Curing the curable composition typically has a dwell time of 0.1 second and 50 seconds; alternatively 1 second to 10 seconds; and alternatively 0.5 second to 30 seconds. Dwell time selected may depend on the substrate selection, temperature selected, and line speed. Dwell time, as used herein, refers to the time during which the curable composition, or wet deposit, is subjected to the elevated temperature. Dwell time is distinguished from cure time, as there may be ongoing curing even after the curable composition, wet deposit, or partially cured reaction intermediary thereof is no longer subjected to the elevated temperature, which typically initiates curing. In certain embodiments, the coated article is prepared on a conveyor belt in an oven, and the dwell time may be calculated by dividing a length of the oven (e.g. in meters) by a line speed of the conveyor belt (e.g. in meters/sec).

The period of time may be broken down into cure iterations, e.g. a first-cure and a post-cure, with the first-cure being, for example, one hour and the post cure being, for example, three hours. The elevated temperature may be independently selected from any temperature above room temperature in such iterations, and may be the same in each iteration.

Depending on a thickness and other dimensions of the film and coated substrate, the coated substrate can be formed via an iterative process. For example, a first deposit may be formed and subjected to a first elevated temperature for a first period of time to give a partially cured deposit. Then, a second deposit may be disposed on the partially cured deposit and subjected to a second elevated temperature for a second period of time to give a second partially cured deposit. The partially cured deposit will also further cure during exposure to the second elevated temperature for the second period of time. A third deposit may be disposed on the second partially cured deposit and subjected to a third elevated temperature for a third period of time to give a third partially cured deposit. The second partially cured deposit will also further cure during exposure to the second elevated temperature for the second period of time. This process may be repeated, for example, from 1 to 50 times, to build the coated article as desired. A composite is of partially cured layers may be subjected to a final post-cure, e.g. at the elevated temperature and period of time above. Each elevated temperature and period of time may be independently selected and may be the same as or different from one another. When the article is formed via the iterative process, each deposit may also be independently selected and may differ in terms of starting materials selected in the curable composition, their amounts, or both. Alternatively still, each iterative layer may be fully cured, rather than only being partially cured, in such an iterative process.

In certain embodiments, the deposit comprises a wet film. In these embodiments, the iterative process may be wet-on-wet, depending on a cure state of the partially cured layer. Alternatively, the iterative process may be wet-on-dry.

The coated substrate, which comprises the film formed from the curable composition on the substrate, may have varying dimensions, including relative thicknesses of the film and the substrate. The film has a thickness that may vary depending upon its end use application. Typically, the film has a thickness of from greater than 0 to 4,000 micrometers (μm), alternatively from greater than 0 to 3,000 μm, alternatively from greater than 0 to 2,000 μm, alternatively from greater than 0 to 1,000 μm, alternatively from greater than 0 to 500 μm, alternatively from greater than 0 to 250 μm. However, other thicknesses are contemplated, e.g. from 0.1 to 200 μm. For example, the thickness of the film may be from 0.2 to 175 μm; alternatively from 0.5 to 150 μm; alternatively from 0.75 to 100 μm; alternatively from 1 to 75 μm; alternatively from 2 to 60 μm; alternatively from 3 to 50 μm; alternatively from 4 to 40 μm; alternatively any one of 1, 2, 3, 4, 5, 6, 7, 8, 9, 10, 15, 20, 25, 30, 35, 40, 45, 50, 60, 70, 75, 80, 90, 100, 150, 175, and 200 μm. In specific embodiments in which the substrate is plastic, the film has a thickness of from greater than 0 to 200, alternatively from greater than 0 to 150, alternatively from greater than 0 to 100, μm. In specific embodiments when the substrate is paper, and when the curable composition is formed as an emulsion, the film has a thickness of from greater than 0 to 20, alternatively from greater than 0 to 15, alternatively from greater than 0 to 10, alternatively from 0.2 to 5.0, μm.

If desired, the film may be subjected to further processing depending upon its end use application. For example, the film may be subjected to oxide deposition (e.g. $SiO_2$ deposition), resist deposition and patterning, etching, chemical, corona, or plasma stripping, metallization, or metal deposition. Such further processing techniques are generally known. Such deposition may be chemical vapor deposition (including low-pressure chemical vapor deposition, plasma-enhanced chemical vapor deposition, and plasma-assisted chemical vapor deposition), physical vapor deposition, or other vacuum deposition techniques. Many such further processing techniques involve elevated temperatures, particularly vacuum deposition, for which the film is well suited in view of its excellent thermal stability. Depending on an end use of the film, however, the film may be utilized with such further processing.

The coated substrate may be utilized in diverse end use applications. For example, the coated substrate may be utilized in coating applications, packaging applications, adhesive applications, fiber applications, fabric or textile applications, construction applications, transportation applications, electronics applications, electrical applications, photonics applications, etc. However, the curable composition may be utilized in end use applications other than preparing the coated substrate, e.g. in the preparation of articles, such as silicone rubbers.

Alternatively, the coated substrate may be utilized as a release liner, e.g. for a tape or adhesive, including any pressure-sensitive adhesives, including acrylic resin-type pressure-sensitive adhesives, rubber-type pressure-sensitive adhesives, and silicone-type pressure-sensitive adhesives, as well as acrylic resin-type adhesives, synthetic rubber-type adhesives, silicone-type adhesives, epoxy resin-type adhesives, and polyurethane-type adhesives. Each major surface of the substrate may having a film disposed thereon for double sided tapes or adhesives.

Alternatively, when the curable composition will be formulated as a release coating composition, the release coating composition may be prepared by mixing the starting materials together, for example, to prepare a one part composition. However, it may be desirable to prepare a release coating composition as a multiple part composition, in which starting materials B) and C) are stored in separate parts, until the parts are combined at the time of use (e.g., shortly before application to a substrate).

For example, a multiple part composition may comprise:

Part (A) a base part comprising A) polyorganosiloxane having an average, per molecule, of at least 2 silicon bonded hydrocarbon groups having terminal aliphatic unsaturation and C) the hydrosilylation reaction catalyst, and when present, one or more of, E) the polydiorganosiloxane having terminally aliphatically unsaturated groups, F) the anchorage additive, and G) the solvent, and Part (B) a curing agent part comprising A) the polyorganosiloxane having an average, per molecule, of at least 2 silicon bonded hydrocarbon groups having terminal aliphatic unsaturation and B) the polyorganohydrogensiloxane, and when present F) the anchorage additive, G) the solvent, or both F) and G). Starting material D), the 2-substituted-1-alkynyl-1cyclohexanol may be added to either Part (A), Part (B), or both. Part (A) and Part (B) may be combined in a weight ratio (A):(B) of 1:1 to 10:1, alternatively 1:1 to 5:1, and alternatively 1:1 to 2:1. Part (A) and Part (B) may be provided in a kit with instructions, e.g., for how to combine the parts to prepare the release coating composition, how to apply the release coating composition to a substrate, and how to cure the release coating composition.

Alternatively, when the anchorage additive is present, it can be incorporated in either of Part (A) or Part (B), or it can be added in a separate (third) part.

Alternatively, the release coating composition may be prepared by a method comprising:
1) mixing starting materials comprising A) the polyorganosiloxane having an average, per molecule, of at least 2 silicon bonded hydrocarbon groups having terminal aliphatic unsaturation, B) the polyorganohydrogensiloxane, C) the catalyst, D) the 2-substituted-1-alknyl-1-cyclohexanol, and optionally one or more of the E) polydiorganosiloxane having an average of one or more terminally aliphatically unsaturated groups per molecule, F) the anchorage additive, and G) the solvent, thereby forming a mixture;
2) applying the mixture on a substrate. Step 1) may be performed by mixing Part (A) and Part (B) of a multiple part composition, as described above.

The release coating composition can for example be applied to the substrate by any convenient means such as spraying, doctor blade, dipping, screen printing or by a roll coater, e.g. an offset web coater, kiss coater or etched cylinder coater.

The release coating composition of the invention can be applied to any substrate, such as those described above. Alternatively, the release coating composition may be applied to polymer film substrates, for example polyester, particularly polyethylene terephthalate (PET), polyethylene, polypropylene, or polystyrene films. The release coating composition can alternatively be applied to a paper substrate, including plastic coated paper, for example paper coated with polyethylene, glassine, super calender paper, or clay coated kraft. The release coating composition can alternatively be applied to a metal foil substrate, for example aluminum foil.

The method may further comprise: 3) treating the substrate before coating the mixture on the substrate. Treating the substrate may be preformed by any convenient means such as a plasma treatment or a corona discharge treatment. Alternatively, the substrate may be treated by applying a primer. In certain instances anchorage of the release coating may be improved if the substrate treated before coating.

The method may further comprise: 4) removing solvent, which may be performed by any conventional means, such as heating at 50° C. to 100° C. for a time sufficient to remove all or a portion of the solvent. The method may further comprise 5) curing the release coating composition to form a release coating on a surface of the substrate. Curing may be performed by any conventional means such as heating at 100° C. to 200° C.

Under production coater conditions, cure can be effected in a residence time of 1 second to 6 seconds, alternatively from 1.5 seconds to 3 seconds, at an air temperature of 120° C. to 150° C. Heating for steps 4) and/or 5) can be performed in an oven, e.g., an air circulation oven or tunnel furnace or by passing the coated film around heated cylinders.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, different, special, and/or unexpected results may be obtained from each member of the respective Markush group independent from all other Markush members. Each member of a Markush group may be relied upon individually and or in combination and provides adequate support for specific embodiments within the scope of the appended claims.

Furthermore, any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

EXAMPLES

These examples are intended to illustrate some embodiments of the invention to one skilled in the art and are not to be interpreted as limiting the scope of the invention set forth in the claims. The following abbreviations were used: RF: Release Force (Release Tester), CW: Coat Weight (Oxford XRF), DSC: Differential Scanning calorimetry, RO: Rub Off (Anchorage performance), THF: Tetrahydrofuran, and SAS: Subsequent Adhesion Strength (Migration performance).

RT: Room temperature of 25° C. The starting materials used in these examples are as described below. Unless otherwise indicated, viscosity is measured at 25° C.

TABLE 1

Starting Materials A) and B)

| Starting Material | Chemical Structure | Mn (Da) | SiH % | Vinyl % | Viscosity (mPa · s) @ 25° C. |
|---|---|---|---|---|---|
| A1) | Si{[OSi(CH$_3$)$_2$]$_v$—OSi(CH$_3$)$_2$CH=CH$_2$}$_4$ | 12300 | | 0.90 | 345 |
| B1) | (CH$_3$)$_3$Si{—[O—Si(CH$_3$)H]$_{42}$—[O—Si(CH$_2$)$_2$]$_{18}$—}OSi(CH$_3$)$_3$ | 4023 | 1.05 | | 30 |
| B2) | (CH$_3$)$_3$Si{—[O—Si(CH$_3$)H]$_{25}$—}OSi(CH$_3$)$_3$ | 1666 | 1.5 | | 10 |

In Table 1 above, Mn refers to number average molecular weight. In starting material A1), each subscript v independently has a value, where a product (4*v) is sufficient to give the material the Mn shown. Starting material C1) was Karstedt's catalyst.

TABLE 2

—Starting Material D)

| Name | Structure | Melting point (C) | Boiling point (C) |
|---|---|---|---|
| ETCH | 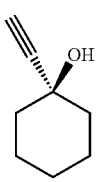 | 30-33 | 180 |

TABLE 2-continued

Starting Material D)

| Name | Structure | Melting point (C) | Boiling point (C) |
|------|-----------|-------------------|-------------------|
| D1-1) | 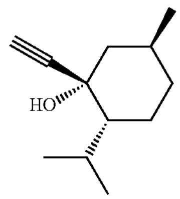 | <-50 | 225 |
| D1-2) | 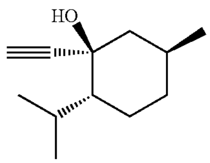 | <-50 | 229 |
| D2) | 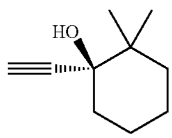 | <-50 | 184 |

In this example 1, 2-isopropyl-4-methyl-1-ethynyl-1-cyclohexanol was prepared, as follows. To a 1 L flask containing ethynylmagnesium bromide solution (0.5 M in THF, 389 ml), was slowly added (−) menthone (28 mL) at 0° C. under $N_2$. The (−)menthone was commercially available from Sigma Aldrich. The ethynyl magnesium bromide was available from Sigma Aldrich. After addition, the mixture was allowed to warm up to RT and stirred for 2 days. Then it was cooled to 0° C., and quenched carefully with addition of aqueous saturated $NH_4Cl$ (10 mL). The mixture was concentrated with a rotary evaporator. The residue was extracted with ethyl acetate (50 mL×3). The combined acetate solution was washed with brine, dried over $Na_2SO_4$, and concentrated with the rotary evaporator to give the crude (d.r.: 3:1). The crude was further purified by vacuum distillation to give a mixture of isomers D1-1 and D1-2 as a colorless liquid. The crude was also be purified by flash chromatography on silica gel eluting with hexanes, hexanes/ethyl acetate (30:1 to 10:1) to give pure D1-1 and D1-2.

D1-1: $^1$H NMR (400 MHz, $CDCl_3$): 2.44 (s, 1H), 2.40 (m, 1H), 1.95 (m, 1H), 1.73 (m, 2H), 1.59 (s, 1H), 1.52-1.28 (m, 5H), 0.96 (d, J=8 Hz, 3H), 0.93 (d, J=8 Hz, 3H), 0.87 (d, J=8 Hz, 3H).

D1-2: $^1$H NMR (400 MHz, $CDCl_3$): 2.48 (s, 1H), 2.16 (m, 1H), 2.08 (s, 1H), 195 (m, 1H), 1.80-1.65 (m, 3H), 1.30-1.17 (m, 3H), 0.99 (d, J=8 Hz, 3H), 0.98 (d, J=8 Hz, 3H), 0.91 (d, J=8 Hz, 3H), 0.88 (m, 1H).

In this example 2, a 500 mL flask was placed in a glovebox. The flask contained a suspension of lithium acetylide ethylenediamine complex (9.5 gram) in 150 mL anhydrous THF at room temperature, and to this was slowly added (−) menthone (16 mL). After addition, the mixture was stirred for 2 hours, then the flask was taken out of the glovebox, cooled to −78° C., and quenched carefully with addition of aqueous saturated $NH_4Cl$ (10 mL). The mixture was concentrated with a rotary evaporator. The residue was extracted with ethyl acetate (50 mL×3). The combined acetate solution was washed with brine, dried over $Na_2SO_4$, and concentrated with the rotary evaporator to give the crude (d.r.: 1:1.5). The crude was further purified by silica gel flash chromatography to give a mixture of D1-1 and D1-2 as colorless liquid (15.8 gram, 95% yield).

In this example 3: to a 1 L flask containing ethynyltrimethylsilane (24.7 mL) in 400 mL anhydrous THF, was slowly added n-butyl lithium (2.5 M in hexanes, 74.6 mL) at −78° C. under $N_2$. After addition, the mixture was stirred for 1 hour, and (−) menthone (28 mL) was slowly added. The mixture was stirred for another 4 hours, then quenched carefully with addition of aqueous saturated $NH_4Cl$ (20 ml). THF was removed with rotary evaporator, and the residue was extracted with ethyl acetate (50 ml×3). The combined acetate solution was washed with brine, dried over $Na_2SO_4$, and concentrated with a rotary evaporator to give the crude, which was used for next step without purification. This produced a solution of crude.

$K_2CO_3$ (44 grams) in methanol (400 mL) was added to the solution of the crude at 0° C., and the mixture was stirred at 0° C. for 6 hours. Methanol was then removed with a rotary evaporator. To the residue, was added water (200 mL), then it was extracted with ethyl acetate (50 mL×3). The combined acetate solution was washed with brine, dried over $Na_2SO_4$, and concentrated with the rotary evaporator to give the crude (d.r. 5:1), which was further purified by vacuum distillation to give a mixture of D1-1 and D1-2 as a colorless liquid.

In this example 4, 2,2-dimethyl-1-ethynyl-1-cyclohexanol was prepared as follows. In a first step, to a 1 L two-neck flask equipped with a water-cooled condenser, was added NaH (60% in mineral oil, 16 gram) and 350 mL anhydrous THF under $N_2$. To this suspension, was added 2-methylcyclohexanone (44 ml). The 2-methylcyclohexanone and the other starting materials were commercially available from Sigma Aldrich. The mixture was heated to reflux for 1.5 hours. $H_2$ gas was released in the first 20 minutes), then HMDS (hexamethyldisilazane, 11.4 mL) was added, and the mixture was refluxed for another 15 minutes. After cooling to 0° C., methyl iodide (30 mL) was slowly added to the flask, and the resulting reaction was highly exothermic. The flask was allowed to warm up to room temperature and stirred for 3 hours. THF was removed with a rotary evaporator. To the residue, was added diethyl ether (150 mL). The mixture was filtered, and ether was removed with the rotary evaporate to give the crude, which was further purified by vacuum distillation to give 2,2-dimethylcyclohexanone as a colorless liquid (37.6 gram, 83% yield).

In a second step, to a 1 L flask containing ethynylmagnesium bromide solution (0.5 M in THF, 350 mL), was slowly added (−) menthone (16.5 gram) at 0° C. under $N_2$. After addition, the mixture was allowed to warm up to room temperature and stirred for 3 hours. Then it was cooled to 0° C., and quenched carefully with addition of aqueous saturated $NH_4Cl$ (10 mL). THF was removed with a rotary evaporator. The residue was extracted with ethyl acetate (50 mL×3). The combined acetate solution was washed with brine, dried over $Na_2SO_4$, and concentrated with the rotary evaporator to give the crude, which was further purified by flash chromatography on silica gel to yield D2) as colorless liquid (14 gram, 70% yield). $^1$H NMR (400 MHz, $CDCl_3$): 2.45 (s, 1H), 1.85-1.35 (m, 8H), 1.09 (s, 3H), 1.01 (s, 3H).

In this example 5, the 2-substituted-1-alkynyl-1-cyclohexanols prepared as described above in examples 1-4 were used as inhibitors in hydrosilylation reaction curable release coating compositions. ETCH was used as an inhibitor in a comparative hydrosilylation reaction curable release coating composition. Release coating composition samples were prepared as follows. Starting materials A1) and B1) and an inhibitor, in amounts shown below in Table 3 were mixed well at room temperature. The relative amounts of A1) and B1) were sufficient to provide a molar ratio SiH/Vi of 2/1. Then, starting material C1), Karstedt's catalyst was then introduced into the flask in an amount sufficient to provide 100 ppm of platinum metal to the release coating composition, and the mixture was mixed well. Starting material C1) and the inhibitor were added in amounts to make a molar ratio of inhibitor/Pt metal of 32/1.

These samples were then evaluated by DSC. The highest reaction peak temperature (Tpeak) and reaction enthalpy (ΔH) are shown in Table 3. Tpeak decreased in order of ETCH, D1-1, D1-2 and D2. The temperature difference between the highest Tpeak—105.83° C., which was demonstrated by ETCH based system, and the lowest Tpeak—91.22° C., which is shown by D2 based system, was on the order of 15° C., which was significant. From a reaction thermodynamics perspective, lower Tpeak means lower energy barrier and higher reactivity. More important, the reaction enthalpy of the four samples was pretty similar, which without wishing to be bound by theory is thought means the reaction type remains the same. System reactivity increased in the order of ETCH, D1-1, D1-2 and D2. Therefore, without wishing to be bound by theory, it is thought that the new inhibitor based systems will cure much faster than the ETCH based system due to their high reactivity, resulting in better cure performance.

TABLE 3

| Starting Material (amounts in grams) and test results | Sample 1 (comparative) | Sample 2 | Sample 3 | Sample 4 |
|---|---|---|---|---|
| A1) | 412.68 | 412.68 | 412.68 | 412.68 |
| B1) | 27.74 | 27.74 | 27.74 | 27.74 |
| C1) | 8.66 | 8.66 | 8.66 | 8.66 |
| D1-1) | 0 | 1.33 | 0 | 0 |
| D1-2) | 0 | 0 | 1.33 | 0 |
| D2) | 0 | 0 | 0 | 1.12 |
| ETCH | 0.92 | 0 | 0 | 0 |
| Pt level | 100 | 100 | 100 | 100 |
| Inhibitor/Pt (mol/mol) | 32 | 32 | 32 | 32 |
| T(peak) ° C. | 105.83 | 101.21 | 97.93 | 91.22 |
| ΔH (J/g) | 42.75 | 42.11 | 43.05 | 43.28 |

A trial was then conducted in a pilot coater by making samples as described below in Table 4, Curing conditions were: curing temperature (oven temperature)—85° C. and dwell time—4 s. The substrate was BOPP C200 from Innovia.

The result is shown in Table 4. It can be seen the samples containing the new inhibitors demonstrated better cure at relatively low cure temperature compared with samples containing ETCH when the same inhibitor/Pt molar ratio and the same platinum catalyst were used, therefore, without wishing to be bound by theory it is thought that the new inhibitors described herein can be used to improve the cure performance of hydrosilylation reaction based release coatings.

TABLE 4

|  | Sample 1 | Sample 2 | Sample 3 | Sample 4 |
|---|---|---|---|---|
| Extractable % | 38.26 | 29.34 | 34.26 | 28.22 |
| ROR % | 18.18 | 25.00 | 12.40 | 30.21 |

In this example 6, the 2-substituted-1-alkynyl-1-cyclohexanols prepared as described above in examples 1-4 were used as inhibitors in hydrosilylation reaction curable release coating compositions. ETCH was used as an inhibitor in a comparative hydrosilylation reaction curable release coating composition. Release coating composition samples were prepared as follows. Starting materials A1) and B2) and an inhibitor, in amounts shown below in Table 5 were mixed well at room temperature. The relative amounts of A1) and B2) were sufficient to provide a molar ratio SiH/Vi of 1.75/1. Then, starting material C1), Karstedt's catalyst was added in an amount sufficient to provide 64.6 ppm of platinum metal to the release coating composition and mixture was mixed well at RT. Starting material C1) and the inhibitor were added in amounts to make a molar ratio of inhibitor/Pt metal of 57.3/1.

First, all samples with compositions shown in Table 5 were tested by DSC. DSC demonstrated a trend with these samples as follows: $T_{peak}$ decrease in the order of sample 5 (ETCH based), sample 6 (Mixture of D1-1) and D1-2), 5/1 mol/mol based), sample 7 (Mixture of D1-1) and D1-2), 3.5/1 mol/mol based) and sample 8 (D2 based), indicating the system reactivity difference between the four systems based on: sample 5 (ETCH based)<sample 6 [Mixture of D1-1] and D1-2] 5/1 mol/mol based]<sample 7 [Mixture of D1-1] and D1-2], 3.5/1 mol/mol based]<sample 8 (D2 based) when the same polymer, crosslinker, catalyst, SiH/Vi molar ratio, Pt level and cure conditions were used. Similarly to the system discussed above, the temperature difference between the highest Tpeak—118.28° C., which was demonstrated by sample 5 (ETCH based), and the lowest Tpeak—103.00° C., which was shown by sample 8 (D2 based), was 15° C. This observation confirmed that the new inhibitors had advantages on cure reactivity.

Bulk Bath Life was measured as follows. The initial viscosity was measured by Brookfield DV-II viscometer with the appropriate spindle at 40° C. After 1, 2, 3 and 4 hours, the viscosity was measured accordingly. The bulk bath life was considered as the time when the viscosity of the mixture doubled as compared to the initial viscosity. In terms of bulk bath life, all four samples afforded bath life much longer than 4 hours (Table 5). In terms of viscosity at 4 hours, sample 5 (ETCH based) demonstrated the lowest viscosity (166 cPs), sample 8 (D2 based) showed the highest viscosity (181 cPs) and two other samples are were as follows: sample 6 [Mixture of D1-1] and D1-2] 5/1 mol/mol based]—168 cPs and sample 7 [Mixture of D1-1] and D1-2], 3.5/1 mol/mol based]—175 cPs. Since the viscosity increase reflected the system reactivity, this result indicated that the system reactivity increased in the order of sample 5 (ETCH based)<sample 6 [Mixture of D1-1] and D1-2], 5/1 mol/mol based]<sample 7 [Mixture of D1-1] and D1-2], 3.5/1 mol/mol based]<sample 8 (D2 based), which agreed with the conclusion made based on DSC investigation. Although the bulk bath life of each new inhibitor based systems (i.e., the compositions in samples 6-8) were each shorter than sample 5 (ETCH based), the bulk bath life of the systems containing new inhibitors was still suitable for release coating applications.

Thin Film Bath Life was measured as follows. A 2 mil Bird Bar was used to coat the sample on a 1 MIL PET film. The resulting film was checked every 5 minutes. The time when the film became smudged or partially cured was defined as the thin film bath life of the release coating. A significant difference was observed regarding the thin film bath life: sample 5 (ETCH based) had thin film bath life of 45 mins, sample 6 [Mixture of D1-1] and D1-2] 5/1 mol/mol based] had thin film bath life of 400 mins, sample 7 [Mixture of D1-1] and D1-2], 3.5/1 mol/mol based] had thin film bath life of 370 mins, and sample 8 (D2 based) had thin film bath life of 90 mins. Even the most reactive sample 8 (D2 based)

yielded twice as long thin film bath life compared with the least reactive sample 5 (ETCH based), indicating the new inhibitors had a better balanced bulk bath life and thin film bath life, which is an unexpected benefit over ETCH based systems.

The four samples listed in Table 5 were also screened on a pilot coater with the following curing conditions: oven temperature of 143° C.; Dwell time of 1.2 second. As shown by Table 5, sample 6 [Mixture of D1-1] and D1-2] 5/1 mol/mol based], sample 7 [Mixture of D1-1] and D1-2], 3.5/1 mol/mol based] and sample 8 (D2 based) gave better extractable % compared with sample 5 (ETCH based). Sample 8 (D2 based) afforded the lowest extractable %, i.e., 14% lower than sample 5 (ETCH based). In terms of ROR %, similarly, all three new inhibitors demonstrated improved ROR % over that of the sample 5 (ETCH based), meaning better anchorage to substrates. Sample 6 [Mixture of D1-1] and D1-2] 5/1 mol/mol based], sample 7 [Mixture of D1-1] and D1-2], 3.5/1 mol/mol based] and sample 8 (D2 based) afforded better cure performance compared with sample 5 (ETCH based) when the same A) polymer, B) crosslinker, C) catalyst, SiH/Vi molar ratio, Pt level and cure conditions were used.

TABLE 5

| Starting Material (amounts in grams) and test results | Sample 5 (comparative) | Sample 6 | Sample 7 | Sample 8 |
|---|---|---|---|---|
| A1) | 132.7 | 132.7 | 132.7 | 132.7 |
| B2) | 5.30 | 5.30 | 5.30 | 5.30 |
| C1) | 1.74 | 1.74 | 1.74 | 1.74 |
| Mixture of D1-1) and D1-2), 5/1 mol/mol | 0 | 0.479 | 0 | 0 |
| Mixture of D1-1) and D1-2), 3.5/1 mol/mol | 0 | 0 | 0.470 | 0 |
| D2) | 0 | 0 | 0 | 0.405 |
| ETCH | 0.33 | 0 | 0 | 0 |
| Pt level (ppm) | 64.62 | 64.62 | 64.62 | 64.62 |
| Inhibitor/Pt (mol/mol) | 57.24 | 57.24 | 57.24 | 57.24 |
| T(peak) ° C. | 118.29 | 112.25 | 111.41 | 103.00 |
| ΔH (J/g) | 46.68 | 43.91 | 44.27 | 47.48 |
| Bulk bath life (hrs) | >4 | >4 | >4 | >4 |
| Four hrs viscosity at 40° C. | 166 | 168 | 175 | 181 |
| Thin film bath life (mins) | 45 | ≥400 | ≥370 | 90 |
| Extractable % | 36.33 | 24.12 | 27.16 | 22.33 |
| ROR % | 44.35 | 58.16 | 70.26 | 66.08 |

As discussed above, a relatively high level of ETCH is used in a release coating composition when used in a coating bath to achieve good thin film bath life due to ETCH having a very short thin film bath life. Without wishing to be bound by theory, it is thought that an unexpected benefit of the invention herein is that the new inhibitors provide release coating compositions with balanced bath life in that bulk bath life is comparable to release coating compositions containing ETCH and thin film bath life is much longer than release coating compositions ETCH, when the other starting materials (i.e., other than the inhibitor) in the release coating composition are comparable. Thus, in theory, when new inhibitors are used, lower inhibitor level (or lower inhibitor/Pt ratio) can be used to achieve the similar thin film bath life and bulk bath life compared with ETCH. Lower inhibitor level (or lower inhibitor/Pt ratio) may result in better reactivity and better cure performance. This example is used to illustrate this unexpected benefit. In order to do the comparison, the acceptable bulk bath life was selected to be 4 hours, and the acceptable thin film bath life was 45 minutes, as shown by the ETCH based control system, i.e., sample 9 in Table 6. Only the coating systems (release coating compositions) meeting both requirements were considered as acceptable from a bath life perspective and were further compared on a pilot coater from a cure performance perspective.

In this example 7, the 2-substituted-1-alkynyl-1-cyclohexanols prepared as described above in examples 1-4 were used as inhibitors in hydrosilylation reaction curable release coating compositions. ETCH was used as an inhibitor in a comparative hydrosilylation reaction curable release coating composition. Release coating composition samples were prepared as follows. Starting materials A1) and B2) and an inhibitor, in amounts shown below in Table 6 were mixed well at room temperature. The relative amounts of A1) and B2) were sufficient to provide a molar ratio SiH/Vi of 1.75/1. Then, starting material C1), Karstedt's catalyst was added in an amount sufficient to provide the level of platinum metal shown in Table 6 to the release coating composition and mixture was mixed well at RT. Starting material C1) and the inhibitor were added in amounts to make the molar ratio of inhibitor/Pt metal as shown in Table 6. Clearly, under the premise of 4 hours bulk bath life and 45 mins thin film bath life, sample 9 (ETCH based) needed high inhibitor/Pt ratio (57.24/1 mol/mol), while sample 10 [Mixture of D1-1] and D1-2] 5/1 mol/mol based], sample 11 [Mixture of D1-1] and D1-2], 3.5/1 mol/mol based] and sample 12 (D2 based) needed much less: sample 10 [Mixture of D1-1] and D1-2] 5/1 mol/mol based]—25.09/1 (mol/mol); sample 11 [Mixture of D1-1] and D1-2], 3.5/1 mol/mol based]—25.09/1 (mol/mol); sample 12 (D2 based)—33.25/1 (mol/mol). Without wishing to be bound by theory, it is thought that it would be possible to lower the inhibitor/Pt ratio for sample 10 [Mixture of D1-1] and D1-2] 5/1 mol/mol based] and sample 12 (D2 based) because each of their bulk bath life was still longer than the required 4 hours. Sample 9-12 were tested on a pilot coater. The curing condition used were: oven temperature—143° C.; Dwell time—1.2 second. The result is shown in Table 6. The new inhibitor based release coating samples 10-11 demonstrated much better extractable % and ROR % than ETCH based sample 9, indicating the new inhibitors can improve the cure performance greatly under the same requirement of thin film bath life and bulk bath life compared with ETCH. Without wishing to be bound by theory, it is thought that the lower the extractable %, and the higher the ROR % is, the better the cure performance is of the release coating.

After showing that the new inhibitors could improve cure performance under the conditions tested for thin film bath life and bulk bath life compared with ETCH, the capability of the new inhibitors to lower the Pt usage was investigated. The study was performed in this way: The Pt level in the ETCH based system (sample 9) was increased gradually to determine the level at which the extractable % and ROR % were similar to the cure performance of sample 11 [Mixture of D1-1] and D1-2], 3.5/1 mol/mol based], which indicated how much more Pt was needed to achieve similar cure performance as sample 11 [Mixture of D1-1] and D1-2], 3.5/1 mol/mol based]. As shown in table 6, when Pt increased from 64.62 ppm to 87 ppm, the cure performance of the comparative ETCH based system was close to the cure performance of sample 11 [Mixture of D1-1] and D1-2], 3.5/1 mol/mol based]. Note: the value was estimated based on the extractable % and ROR % of samples 13 and 14. In other words, the new inhibitor [Mixture of D1-1] and D1-2], 3.5/1 mol/mol based] can save about 22 ppm Pt, which is a significant reduction if the overall Pt level is considered due to the high cost and limited commercial availability of Pt.

The ROR % test (sometimes referred to as anchorage index) measured the amount of cured silicone left after the coated substrate was subjected to surface abrasion. It indicated how strong the cured coating film was anchored to the substrate;

TABLE 6

| Starting Material (amounts in grams) and test results | Control (ETCH) Sample 9 (comparative) | New inhibitors with the same Pt level as control system | | | ETCH based systems with different Pt level | | |
|---|---|---|---|---|---|---|---|
| | | Sample 10 | Sample 11 | Sample 12 | Sample 13 | Sample 14 | Sample 15 |
| A1) | 637.15 | 637.15 | 637.15 | 637.15 | 637.15 | 637.15 | 637.15 |
| B2) | 25.44 | 25.44 | 25.44 | 25.44 | 25.44 | 25.44 | 25.44 |
| C1) | 8.37 | 8.37 | 8.37 | 8.37 | 11.03 | 12.32 | 11.66 |
| Mixture of D1-1) and D1-2), 5/1 mol/mol | | 2.30 | | | | | |
| Mixture of D1-1) and D1-2), 3.5/1 mol/mol | | | 2.30 | | | | |
| D2) | | | | 1.94 | | | |
| ETCH | 1.58 | | | | 1.58 | 1.58 | 1.58 |
| Pt level (ppm) | 64.62 | 64.62 | 64.62 | 64.62 | 84.62 | 94.62 | 89.62 |
| Inhibitor/Pt (mol/mol) | 57.24 | 25.09 | 25.09 | 33.25 | 43.06 | 38.99 | 41.17 |
| Bulk bath life (hrs) | >4 | >4 | 4 | >4 | >4 | >4 | >4 |
| Four hrs viscosity at 40° C. (cPs) (initial viscosity = 161 cPs) | 166 | 284 | 320 | 277 | 169 | 173 | 169 |
| Thin film bath life (mins) | 45 | ≥240 | 300 | 100 | ≥30 | ≥30 | ≥30 |
| Extractable % | 36.33 | 15.66 | 13.16 | 20.42 | 17.12 | 9.71 | 9.51 |
| ROR % | 44.35 | 80.28 | 89.55 | 73.71 | 81.09 | 96.64 | 93.73 |

To measure the cure performance of the compositions, an extractable test was undertaken immediately after cure. The extractable test was utilized to identify the amount of non-crosslinked silicone that was extractable from a cured release coating sample in the presence of a solvent. The test method used for the following example was as follows:
1. Immediately upon completion of the coating process (described above) three sample discs were cut from a coated substrate using a 1⅜" (3.49 cm) die cutter.
2. The silicone coat weight on each sample was determined using an Oxford Instruments Lab-X 3500 Benchtop XRF analyzer.
3. Each disc was then placed in an individual 100-mL bottle containing 40 mL of methyl isobutyl ketone solvent. Tweezers were used for handling sample discs at all times to ensure that the silicone surface of the sample was uncontaminated or damaged. The solvent bottles were then covered with lids and allowed to rest on the laboratory bench top for 30 minutes. After this period the discs were removed from the solvent and placed on clean tissue paper, with the silicone coated side up.
4. The solvent was allowed to evaporate from the sample discs without wiping or blotting the samples.
5. The final coat weight of each sample disc was then determined and.
6. The percent of extractable was calculated using the following formula:

$$\text{Extractable } \% = \frac{(W_i - W_f)}{W_i} \times 100\%$$

$W_i$=initial coat weight (before solvent introduction)
$W_f$=final coat weight (after solvent evaporation)

In this example 9, anchorage of the release coating to the substrate was measured as % rub off resistance (ROR %) on samples prepared as described above in Example 7, Table 6. the higher the ROR % value the better. The ROR % was measured as soon as the coated substrate exited the curing oven. From each coated substrate, 2 sample discs were prepared and the silicone present in each sample disc of the coated substrate was then determined via an Oxford Instruments Lab-X 3500 Benchtop XRF analyzer. Each sample disc of the coated substrate was then subjected to an abrasion test under a load of 1.9 kg and in contact with a felt using automated abrading equipment, in a manner similar to a Taber-type method'. The ROR % was calculated as follows: ROR %=($W_f/W_i$)×100, where $W_i$ is the initial coat weight (before abrasion) and $W_f$=final coat weight (after abrasion).

Thin film and bulk bath life tests were conducted as follows:

Thin Film Bath Life was measured as follows. A 2 mil Bird Bar was used to coat the release coating sample on a 1 MIL PET film. The resulting film was checked every 5 minutes. The time when the film became smudged or partially cured was defined as the thin film bath life of the release coating.

Bulk Bath Life was measured as follows: Polymer, crosslinker and inhibitor (150 g) were added to a 250 mL round glass jar and mixed well at room temperature (RT). The capped glass jar was heated in a 40 C water bath for 50-60 mins. Catalyst was added into the mixture quickly and the solution was mixed well. Then, the initial viscosity was measured by Brookfield viscometer (in water bath). The jar was capped. After 1, 2, 3 and 4 hours, the viscosity was measured repeatedly. The bulk bath life was considered as the time when the internal viscosity increased twice compared with the initial viscosity.

Aged anchorage test and release force test were measured as follows:

Aged anchorage test: The release liner samples were aged at RT under constant humidity (RH=51%) and pressure for 2 month.

Release force test: release liner samples were laminated with Tesa 7475 tape and aged at RT under constant humidity (RH=51%) and pressure for 2 months. The laminates were peeled at speed from low to high: 0.3 m/min, 10 m/min, 100 m/min and 200 m/min at 180° angle.

Aged anchorage (ROR %) and aged release force are two other important parameters in the release coating industry. Thus, the impact of the new inhibitors on 2 month aged anchorage (ROR %) and 2 month release force were studied. The aged anchorage of the system based on new inhibitors were similar to that of ETCH based system under the conditions tested herein, as shown in Table 7. The release force of the coatings prepared from samples containing the four inhibitors were comparable to each other. Without wishing to be bound by theory, it is thought that the relatively small difference could be ascribed to the cure degree difference of the release liner samples. Therefore, the new inhibitors did not negatively impact the aged anchorage and release profile as compared to the same release coating composition containing ETCH as the inhibitor instead.

| Test results | Sample 5 | Sample 6 | Sample 7 | Sample 8 | Sample 9 | Sample 10 | Sample 11 | Sample 12 | Sample 13 | Sample 14 | Sample 15 |
|---|---|---|---|---|---|---|---|---|---|---|---|
| 2 month RT aged ROR % | 96.79 | 99.22 | 99.21 | 99.02 | 96.79 | 97.33 | 100 | 100 | 99.21 | 98.21 | 98.35 |
| Release force at 0.3 m/min (cN/25 mm) | 21.17 | 20.30 | 21.57 | 23.73 | 21.17 | 25.60 | 26.53 | 24.10 | 28.63 | 30.60 | 31.23 |
| Release force at 10 m/min (cN/25 mm) | 41.53 | 43.68 | 42.39 | 45.08 | 41.53 | 42.41 | 45.30 | 43.33 | 47.08 | 47.72 | 46.53 |
| Release force at 100 m/min (cN/25 mm) | 64.68 | 64.74 | 63.31 | 69.22 | 64.68 | 69.61 | 70.94 | 67.24 | 69.55 | 72.62 | 68.42 |
| Release force at 300 m/min (cN/25 mm) | 68.86 | 67.48 | 69.57 | 67.67 | 68.86 | 64.20 | 70.19 | 67.01 | 66.46 | 74.14 | 71.18 |

INDUSTRIAL APPLICABILITY

The inventors surprisingly found that adding substituents to an unsubstituted 1-alkynyl-1-cyclohexanol, which must be melted by pre-heating step due to that its melting point is higher RT temperature, decreased the melting point of the resulting 2-substituted-1-alknynyl-1-cyclohexanol to a temperature lower than −50° C., which can make the 2-substituted-1-alknyl-1-cyclohexanol easier to formulate into curable compositions, such as release coating compositions. Without wishing to be bound by theory, it is thought that the 2-substituted-1-alkynyl-1-cyclohexanols described herein are easier to formulate into release coating compositions because pre-heating the polyorganosiloxane, the 2-substituted-1-alknynyl-1-cyclohexanol, or both before mixing is not required to combine the 2-substituted-1-alknynyl-1-cyclohexanol with the other starting materials in the composition, and maintaining the composition at a temperature high enough to prevent unsubstituted inhibitors (such as ETCH) from crystallizing out of the composition is similarly not required.

The release coating compositions including the release coating systems based on 2-substituted-1-alkynyl-1-cyclohexanol as described in the examples above had comparable bulk bath life, much longer thin film bath life and better cure performance as release coating compositions based on ETCH when the same polymer, crosslinker, catalyst, SiH/Vi molar ratio and inhibitor/Pt molar ratio. It means the new 2-substituted-1-alkynyl-1-cyclohexanol are much better inhibitors from bath life, cure speed, and/or compatibility perspectives. Since the new 2-substituted-1-alkynyl-1-cyclohexanol inhibitors have comparable bulk bath life, much longer thin film bath life, much lower inhibitor level (or inhibitor/Pt molar ratio) can be used and thus much better cure performance can be achieved without sacrificing the requirements on thin film bath life and bulk bath life. On the other hand, due to the new 2-substituted-1-alkynyl-1-cyclohexanol inhibitors having comparable bulk bath life and much longer thin film bath life, these can be used in hydrosilylation curable compositions to reduce the expensive Pt catalyst usage significantly without sacrificing the cure performance of the compositions.

The invention claimed is:

1. A curable composition comprises:
   A) a polyorganosiloxane containing at least two silicon-bonded aliphatically unsaturated groups per molecule;
   B) a polyorganohydrogensiloxane having an average, per molecule, of at least 2 silicon bonded hydrogen atoms; with the provisos that
      when starting material A) has an average, per molecule, of 2 silicon aliphatically unsaturated groups, then starting material B) has an average, per molecule, of greater than 2 silicon bonded hydrogen atoms; and
      when starting material B) has an average, per molecule, of 2 silicon bonded hydrogen atoms, then starting material A) has an average, per molecule, of greater than 2 silicon bonded aliphatically unsaturated groups;
   C) a hydrosilylation-reaction catalyst; and
   D) a 2-substituted 1-alkynyl-1-cyclohexanol, where starting material D) has general formula

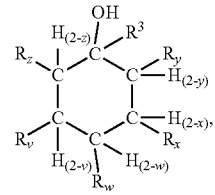

where $R^3$ is an alkynyl group having at least 2 carbon atoms, each R is methyl or isopropyl, subscript v is 0 to 2, subscript w is 0 to 2, subscript x is 0 to 2, subscript y is 0 to 2, subscript z is 0 to 2, with the provisos that a quantity (v+w+x+y+z)>1, and a quantity (y+z) is 1 to 4.

2. The curable composition of claim 1, where Starting material A) comprises a branched siloxane of unit formula $(R^1_3SiO_{1/2})_p(R^2R^1_2SiO_{1/2})_q(R^1_2SiO_{2/2})_r(SiO_{4/2})_s$, where each $R^1$ is independently a monovalent hydrocarbon group free of aliphatic unsaturation or a monovalent halogenated hydrocarbon group free of aliphatic unsaturation and each $R^2$ is an aliphatically unsaturated monovalent hydrocarbon group, subscript p≥0, subscript q>0, 15≥r≥995, and subscript s is >0;

Starting material B) comprises a polyorganohydrogensiloxane of unit formula $(R^6{}_3SiO_{1/2})_{hh}(R^5{}_2SiO_{2/2})_{ii}(R^5HSiO_{2/2})_{jj}$, where each $R^6$ is independently hydrogen or $R^5$, each $R^5$ is a monovalent hydrocarbon group or a monovalent halogenated hydrocarbon group, and subscript hh≥2, subscript ii≥0, and subscript jj≥2;

Starting material C) comprises a platinum catalyst; and the curable composition is a release coating composition.

3. The composition of claim 1, where in starting material D) $R^3$ is an alkynyl group of 2 to 6 carbon atoms, each R is methyl, with the provisos that a quantity (v+w+x)=0, and the quantity (y+z) is 2.

4. The composition of claim 1, where each $R^3$ is an alkynyl group of 2 to 6 carbon atoms, the quantity (y+z) is 1 to 2, and the quantity (v+w+x+y+z) is 1 to 4.

5. The composition of claim 4, where each $R^3$ is ethynyl.

6. The composition of claim 5, where subscript w=1, subscript y=1, and subscripts v=x=z=0.

7. The composition of claim 5, where subscript y=2 and subscripts v=w=x=z=0.

8. The composition of claim 5, where the composition is a release coating composition, and the release coating composition further comprises one or more of E) a polydiorganosiloxane having an average of one or more terminally aliphatically unsaturated groups per molecule, F) an anchorage additive, G) a solvent H) an anti-mist additive, I) a controlled release agent, and J) a colorant.

9. The composition of claim 1, where starting material D) is selected from the group consisting of general formula D1), general formula D2), or both D1) and D2), where:

D1) is

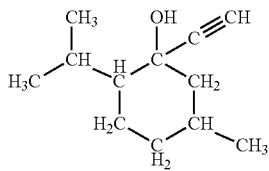

and D2) is

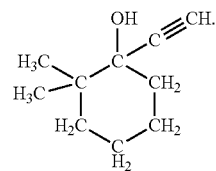

10. The composition of claim 9, where the composition is a release coating composition, and the release coating composition further comprises one or more of E) a polydiorganosiloxane having an average of one or more terminally aliphatically unsaturated groups per molecule, F) an anchorage additive, G) a solvent H) an anti-mist additive, I) a controlled release agent, and J) a colorant.

11. A method for preparing the curable composition of claim 1, where the method comprises: 1) combining starting materials comprising A), B), C) and D) at room temperature of 25° C. or less.

12. The method of claim 11, where step 1) comprises mixing the starting materials, thereby forming a mixture; the curable composition is a release coating composition; and the release coating composition further comprises one or more of E) a polydiorganosiloxane having an average of one or more terminally aliphatically unsaturated groups per molecule, F) an anchorage additive, G) a solvent, H) an anti-mist additive, I) a controlled release agent, and J) a colorant.

13. A method for preparing a release liner comprising: applying the mixture of claim 12 on a substrate and curing the release coating composition.

14. The method of claim 13, further comprising one or both of: treating the substrate before applying the mixture on the substrate and removing solvent before curing the release coating composition.

15. A method for forming a coating a substrate comprising:
1) applying to a substrate a curable composition comprising
A) a polyorganosiloxane containing at least two silicon-bonded aliphatically unsaturated groups per molecule;
B) a polyorganohydrogensiloxane having an average, per molecule, of at least 2 silicon bonded hydrogen atoms;
with the provisos that
when starting material A) has an average, per molecule, of 2 silicon aliphatically unsaturated groups, then starting material B) has an average, per molecule, of greater than 2 silicon bonded hydrogen atoms; and
when starting material B) has an average, per molecule, of 2 silicon bonded hydrogen atoms, then starting material A) has an average, per molecule, of greater than 2 silicon bonded aliphatically unsaturated groups;
C) a hydrosilylation-reaction catalyst; and
D) a 2-substituted 1-alkynyl-1-cyclohexanol, where starting material D) has general formula

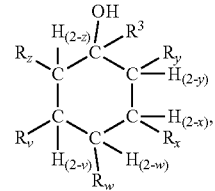

where $R^3$ is an alkynyl group having at least 2 carbon atoms, each R is methyl or isopropyl, subscript v is 0 to 2, subscript w is 0 to 2, subscript x is 0 to 2, subscript y is 0 to 2, subscript z is 0 to 2, with the provisos that a quantity (v+w+x+y+z)>1, and a quantity (y+z) is 1 to 4,
optionally 2) treating the substrate before applying the composition, and 3) heating the composition, thereby curing composition to form the coating on the substrate.

16. A coated substrate prepared by the method of claim 15.

17. The coated substrate of claim 16, where the composition is a release coating composition.

18. The coated substrate of claim 17, where the coated substrate is a release liner.

\* \* \* \* \*